United States Patent [19]

Shen et al.

[11] 4,057,637

[45] Nov. 8, 1977

[54] 5-MERCAPTOPYRIDOXINE ESTERS

[75] Inventors: Tsung-Ying Shen, Westfield; Howard Jones, Holmdel; Dennis M. Mulvey, Milford; Conrad P. Dorn, Plainfield, all of N.J.

[73] Assignee: Merck & Co., Inc., Rahway, N.J.

[21] Appl. No.: 685,211

[22] Filed: May 11, 1976

Related U.S. Application Data

[60] Division of Ser. No. 470,231, May 16, 1974, Pat. No. 3,971,797, which is a continuation-in-part of Ser. No. 368,774, June 15, 1973, abandoned.

[51] Int. Cl.$^2$ .................... A61K 31/44; C07D 213/62
[52] U.S. Cl. ............................ 424/263; 260/294.8 E; 260/294.8 G
[58] Field of Search ................. 260/294.8 E, 294.8 G; 424/263

[56] References Cited

U.S. PATENT DOCUMENTS 3,010,966  11/1961  Zima et al. .................... 260/294.8 E

*Primary Examiner*—Alan L. Rotman
*Attorney, Agent, or Firm*—Raymond M. Speer; Harry E. Westlake, Jr.; Frank M. Mahon

[57] ABSTRACT

Mercaptoalkylpyridines and various derivatives thereof have utility in the treatment of rheumatoid arthritis. The compounds useful in the method of treatment are generally prepared from known pyridine derivatives and, principally, from pyridoxine and related compounds.

6 Claims, No Drawings

5-MERCAPTOPYRIDOXINE ESTERS

This application is a division of prior co-pending application Ser. No. 470,231, filed May 16, 1974, now U.S. Pat. No. 3,971,797, issued July 27, 1976, which in turn is a continuation-in-part of application Ser. No. 368,774, filed June 15, 1973, now abandoned.

This invention is concerned with a method of treating rheumatoid arthritis and related inflammatory diseases with mercaptoalkylpyridines; with some of the compounds which are novel; and with the method of preparation of the novel compounds.

More particularly, it is concerned with the method of treatment of rheumatoid arthritis with a compound of structural formula:

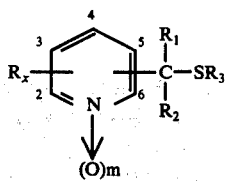

or pharmaceutically acceptable salt thereof, wherein:

$R_1$ is hydrogen, $C_{1-3}$ alkyl or phenyl;
$R_2$ is hydrogen or $C_{1-3}$ alkyl;
$R_3$ is (a) hydrogen, (b) —SO$_3$H, (c) —PO$_3$H$_2$, (d) amidino, (e) N(C$_{1-4}$ alkyl), (f) CH$_2$CH(NH$_2$)COOH (g) ethoxycarbonylmethyl,

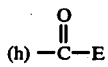

(h) —C—E where E represents (1) adamantyl, (2) $C_{3-8}$ cycloalkyl, (3) $C_{1-5}$ alkoxy, (4) $C_{2-6}$ alkyl, (5) N(C$_{1-4}$ alkyl), (6) phenyl, (7) 2-acetoxyphenyl, (8) 2-hydroxy-4-(2,4-difluorophenyl)phenyl, (9) 3-chloro-4-allyloxybenzyl, (10) α-methyl-4-isobutylbenzyl, (11) α-methyl-3-phenoxybenzyl, (12) α-methyl-3-benzoylbenzyl, (13) 1-(6-methoxynaphth-2-yl)-ethyl, (14) α-methyl-3-fluoro-4-phenylbenzyl, (15) α-methyl-(3-chloro-4-cyclohexylbenzyl), (16) 2-(3-trifluoromethylanilino)phenyl, (17) 2-(2,3-dimethylanilino)phenyl, (18) 2-(2,6-dichloro-3-methylanilino)phenyl, (19) 2-(3-trifluoromethylanilino)-3-pyridyl, (20) 2-(2-methyl-3-chloroanilino)-3-pyridyl, (21) —NH$_2$, or

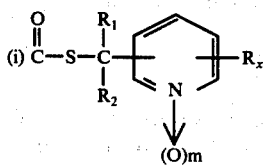

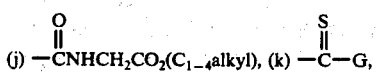

where G represents (1) $C_{1-4}$ alkoxy, (2) —S(alkali metal) or (3)

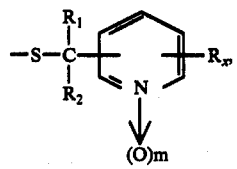

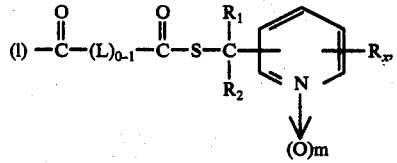

wherein L represents (1) —(CH$_2$)$_{1-5}$, (2) phenylene or

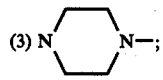

(m) —S—R$^{12}$, wherein R$^{12}$ represents (1) —C(CH$_3$)$_2$CH(NH$_2$) COOH, (2) $C_{1-5}$ alkyl, (3) $C_{2-5}$ alkenyl, (4) phenyl-$C_{1-3}$ alkyl, (5) phenyl, (6) $C_{2-5}$ alkynyl, (7) 2-carboxyphenyl, or (8)

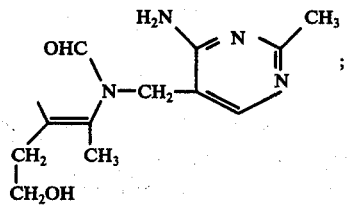

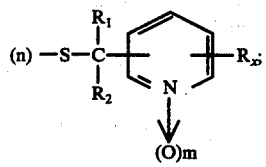

$m$ is 0 or 1;
X is an integer from 0–4; and
R is
(1) 3 or 5 hydroxy,
(2) 3, 5, or 6 $C_{1-3}$ alkoxy,
(3) 3 or 5

where E is as defined above,
(4) 5 carboxy, (5) 5 carbamyl, (6) 4 hydroxyiminomethyl,
(7) 4 formyl,
(8) 2, 3, 4, 5, or 6 $C_{1-5}$ alkyl,
(9) 2, 3, 4, 5, or 6 mercapto-$C_{1-3}$ alkyl,

(10) 3 or 5 —OC—NH$_2$, 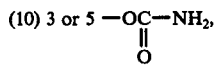

(11) 4 or 5 C$_{1-3}$alkyl—O—CNH$_2$, 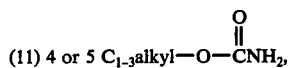

(12) 3 or 5 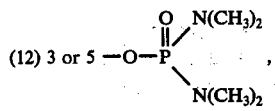

(13) 4 or 5 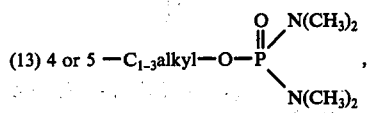

(14) 5 C$_{1-3}$ alkylthio-C$_{1-3}$ alkyl, p3 (15) 4 or 5 hydroxy-C$_{1-3}$ alkyl,
(16) 4 or 5 C$_{1-3}$ alkoxy-C$_{1-3}$ alkyl,
(17) 4 or 5 amino-C$_{1-3}$ alkyl,
(18) 4 or 5 di(C$_{1-3}$ alkyl)amino-C$_{1-3}$ alkyl,
(19) 5 carboxy-C$_{1-3}$ alkyl,
(20) 4 or 5 C$_{1-3}$ alkyl—O—C—E, 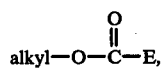

where E is as defined above,
(21) when one R is hydroxy and another R is hydroxymethyl or mercaptomethyl on an adjacent carbon, the oxygens, or oxygen and sulfur, may be joined together through a group, of formula

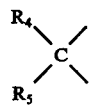

wherein R$_4$ and R$_5$ are the same or different and each is hydrogen, C$_{1-6}$ alkyl or phenyl, or taken together, R$_4$ and R$_5$ represent =O or =S; with the proviso that 5-mercaptopyridoxine and pyrithioxine and pharmaceutically acceptable salts thereof are specifically excluded.

A preferred embodiment of this invention is the novel method of treatment with a compound of formula:

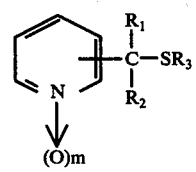

or pharmaceutically acceptable salts thereof, wherein R$_1$, R$_2$, and m are as defined above and R$_3$ is hydrogen, —SO$_3$H, —PO$_3$H$_2$, —SC(CH$_3$)$_2$CH(NH$_2$)COOH, adamantanoyl, benzoyl, C$_{3-8}$ cycloalkycarbonyl, C$_{2-6}$ alkanoyl, or

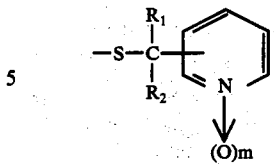

Another preferred embodiment of this invention is the novel method of treatment with a compound of structural formula:

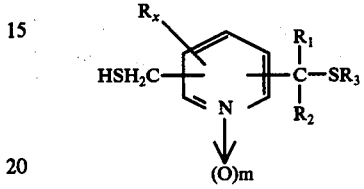

or pharmaceutically acceptable salt thereof, wherein m, R$_1$, and R$_2$ are as defined above; X is an integer from 0 to 3; R$_3$ is hydrogen; —SO$_3$H, —PO$_3$H$_2$, -SC(CH$_3$)$_2$CH(NH$_2$)COOH, adamantanoyl, benzoyl, C$_{3-8}$ cycloalkylcarbonyl, C$_{2-6}$ alkanoyl, or

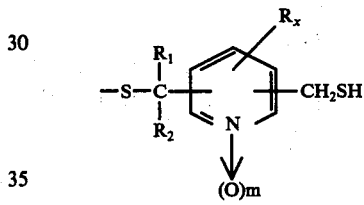

R is
(1) 3 or 5 hydroxy,
(2) 3,5, or 6 C$_{1-3}$ alkoxy,
(3) 3 or 5 C$_{2-6}$ alkanoyloxy,
(4) 3 or 5 benzoyloxy,
(5) 3 or 5 C$_{3-8}$ cycloalkylcarbonyloxy,
(6) 3 or 5 C$_{1-5}$ alkoxycarbonyloxy,
(7) 3 or 5 adamantanoyloxy,
(8) 5 carboxy,
(9) 5 carbamyl,
(10) 4hydroximinomethyl,
(11) 4 formyl,
(12) 2,3,4,5, or 6 C$_{1-5}$ alkyl,
(13) 5C$_{1-3}$ alkylthio-C$_{1-3}$ alkyl,
(14) 4 or 5 hydroxy-C$_{1-3}$ alkyl,
(15) 4 or 5 C$_{1-3}$ alkoxy-C$_{1-3}$ alkyl,
(16) 4 or 5 amino-C$_{1-3}$ alkyl,
(17) 4 or 5 di(C$_{1-3}$ alkyl)amino-C$_{1-3}$ alkyl,
(18) 5 carboxy-C$_{1-3}$ alkyl,
(19) 4 or 5 C$_{2-6}$ alkanoyloxy-C$_{1-3}$ alkyl,
(20) 4or 5 benzoyloxy-C$_{1-3}$ alkyl,
(21) 4 or 5 C$_{3-8}$ cycloalkylcarbonyloxy-C$_{1-3}$ alkyl,
(22) 4 or 5 C$_{1-5}$ alkoxycarbonyloxy-C$_{1-3}$ alkyl,
(23) 4or 5 adamantanoyloxy-C$_{1-3}$ alkyl, and
(24) when one R is hydroxy and another R is hydroxymethyl and mercaptomethyl on an adjacent carbon, the oxygens, or oxygen and sulfur thereof, may be joined together through a group of formula

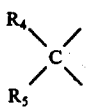

wherein R$_4$ and R$_5$ are as previously defind.

Another preferred embodiment of this invention is the novel method of treatment with a compound of structural formula:

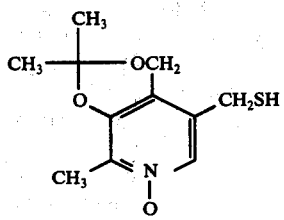

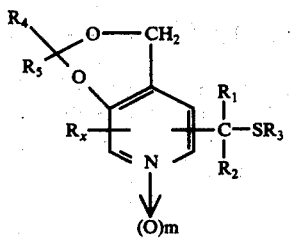

or pharmaceutically acceptable salt thereof, wherein R$_1$, R$_2$, R$_4$, R$_5$ and m are as defined above, X is an integer from 0–2; R$_3$ is hydrogen, —SO$_3$H, —PO$_3$H$_2$,

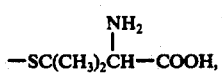

adamantanoyl, C$_{2-6}$ alkanoyl, benzoyl, C$_{3-8}$ cycloalkylcarbonyl, C$_{1-5}$ alkoxycarbonyl, or

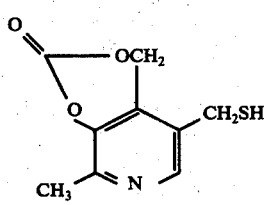

R is
(1) 5 or 6 C$_{1-3}$ alkoxy,
(2) 5 carbamyl,
(3) 2,5, or 6 C$_{1-5}$ alkyl,
(4) 2,5, or 6 mercapto-C$_{1-3}$ alkyl,
(5) 5 C$_{1-3}$ alkylthio-C$_{1-3}$ alkyl,
(6) 5 hydroxy-C$_{1-3}$ alkyl,
(7) 5 C$_{1-3}$ alkoxy-C$_{1-3}$ alkyl,
(8) 5 amino-C$_{1-3}$ aklyl,
(9) 5di(C$_{1-3}$ alkyl)amino-C$_{1-3}$ alkyl,
(10) 5 carboxy-C$_{1-3}$ alkyl,
(11) 5 C$_{2-6}$ alkanoyloxy-C$_{1-3}$ alkyl,
(12) 5 benzoyloxy-C$_{1-3}$ alkyl,
(13) 5 C$_{3-8}$ cycloalkylcarbonyloxy-C$_{1-3}$ alkyl,
(14) 5C$_{1-5}$ alkoxycarbonyloxy-C$_{1-3}$ alkyl,
(15) 5 adamantanoyloxy-C$_{1-3}$ alkyl.

Of particular interest is the method of treatment with the immediately above compounds wherein m is 1, and especially with the compounds of formula

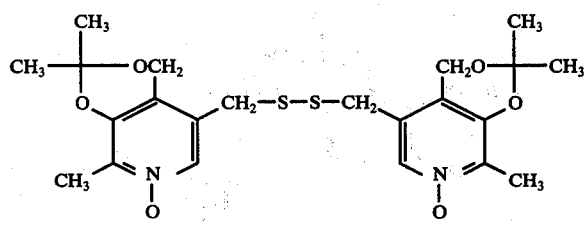

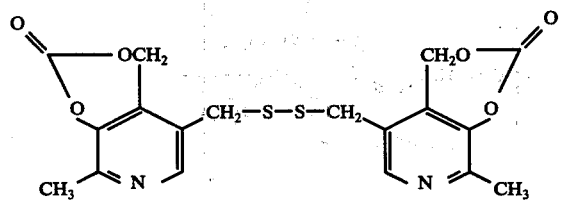

or pharmaceutically acceptable salts thereof.

Another preferred embodiment is the novel method of treatment with a compound of structural formula:

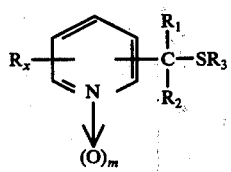

or pharmaceutically acceptable salt thereof, wherein R$_1$, R$_2$, and m are as previously defined, x is 3 and R is C$_{1-3}$ alkyl, 3 or 5

or 4 or 5 -C$_{1-3}$ alkyl

and R$_3$ is

or

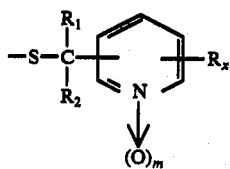

Of particular interest in the above embodiment is the novel method of treatment with the compounds of structure:

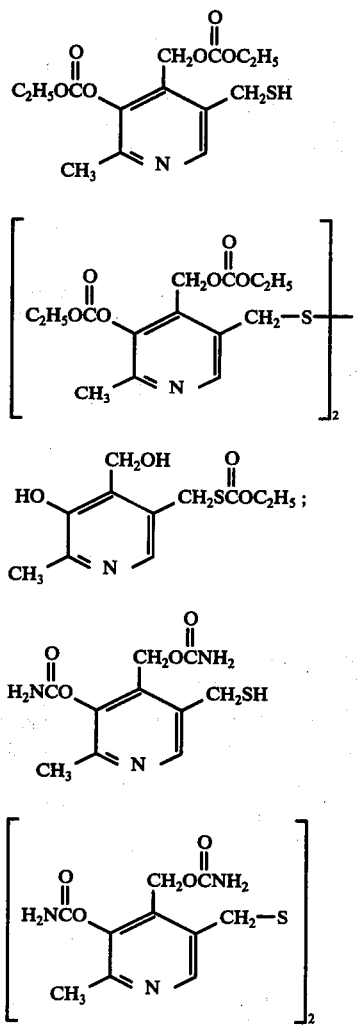

Another preferred embodiment is the novel method of treatment of this invention with a compound of formula:

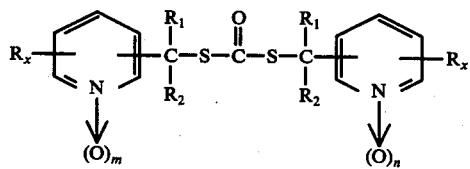

or pharmaceutically acceptable salt thereof, wherein R, $R_1$, $R_2$, x and m are as defined above.

Of particular interest in this class is the compound of formula:

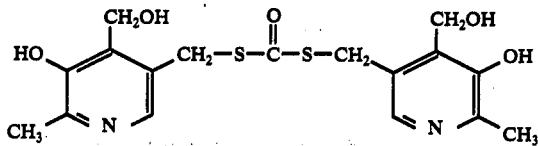

Known compounds that are active in the novel method of treatment of this invention include the following:

2-methyl-3-hydroxy-4-mercaptomethyl-5-hydroxymethylpyridine hydrochloride;
3,4α-di-O-isopropylidene derivative of 5-mercaptopyridoxine hydrochloride;
3-mercaptomethylpyridine hydrochloride;
2-methyl-3-hydroxy-4,5-di(mercaptomethyl)pyridine hydrochloride;
4-mercaptomethylpyridine;
bis [2-methyl-3-hydroxy-4-aminomethyl-5-pyridylmethyl]-disulfide tetrahydrochloride;
2-methyl-3-hydroxy-4-formyl-5-mercaptomethylpyridine hemithioacetal hydrochloride;
2-methyl-3-hydroxy-4-aminomethyl-5-mercaptomethylpyridine and its Bunte salt;
2-methyl-3-acetoxy-4-acetoxymethyl-5-mercaptomethylpyridine;
2-methyl-3-hydroxy-4-mercaptomethyl-5-methylpyridine;
bis[2-methyl-3-hydroxy-5-hydroxymethyl-4-pyridylmethyl]-disulfide.

Another embodiment of this invention is the novel compounds which find utility in the method of treatment. These novel compounds are represented by the following structural formula:

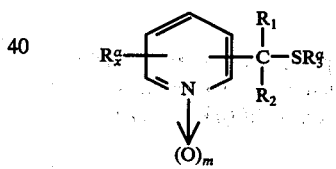

or pharmaceutically acceptable salt thereof, wherein
m is 0 or 1;
$R_1$ is hydrogen, $C_{1-3}$ alkyl or phenyl;
$R_2$ is hydrogen or $C_{1-3}$ alkyl;
$R_3{}^a$ is (a) hydrogen; (b) —$SO_3H$; (c) —$PO_3H_2$; (d) $N(C_{1-4}$ alkyl);

(e) $-\overset{O}{\underset{\parallel}{C}}-E^a$, wherein $E^a$ represents (1) adamantyl, (2) $C_{3-8}$ cycloalkyl, (3) $C_{1-5}$-alkoxy, (4) $C_{2-5}$ alkenyloxy, (5) $N(C_{1-4}$ alkyl), (6) phenyl, (7) 2-acetoxyphenyl, (8) 2-hydroxy-4-(2,4-difluorophenyl)phenyl, (9) 3-chloro-4-allyloxybenzyl, (10) α-methyl-4-isobutylbenzyl, (11) α-methyl-3-phenoxybenzyl, (12) α-methyl-3-benzoylbenzyl, (13) 1-(6-methoxynaphth-2-yl)ethyl, (14) α-methyl-3-fluoro-4-phenylbenzyl, (15) α-methyl-3-chloro-4-cyclohexylbenzyl, (16) 2-(3-trifluoromethylanilino)phenyl, (17) 2-(2,3-dimethylanilino)phenyl, (18) 2-(2,6-dichloro-3-methylanilino)phenyl, (19) 2-(3-trifluoromethylanilino-3-pyridyl, (20) 2-(2-methyl-3-chloroanilino)-3-pyridyl, (f) 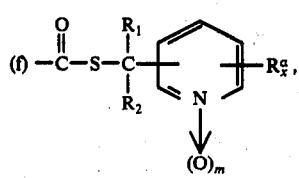

(g) 

(h) 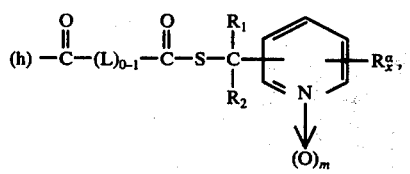

wherein L represents (1) —(CH$_2$)$_{1-5}$—, (2) phenylene, or (3) 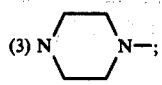

(i) —S—R$_{12}$$^a$, wherein R$_{12}$$^a$ represents (1) —C(CH$_3$)$_2$CH(NH$_2$)COOH, or (2) 2-carboxyphenyl;

(j) 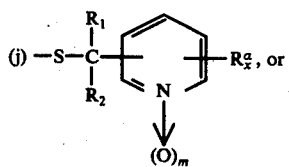, or (k) 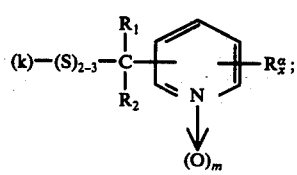;

X is an integer from 0–4; and
R$^a$ is
(1) 3 or 5 hydroxy,
(2) 3, 5, or 6 C$_{1-3}$ alkoxy,
(3) 3 or 5

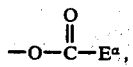, where E$^a$ is as defined above,
(4) 5 carboxy,
(5) 5 carbamyl,
(6) 4 hyroximinomethyl,
(7) 4 formyl,
(8) 2, 3, 4, 5, or 6 C$_{1-5}$ alkyl, (9) 3 or 5 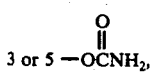,

(10) 4 or 5 —C$_{1-3}$ alkyl—O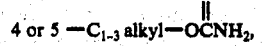,

(11) 3 or 5 —O—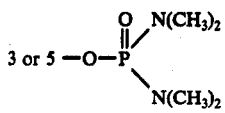

(12) 4 or 5 —C$_{1-3}$ alkyl—O—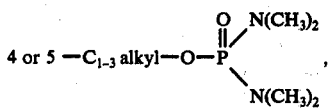,

(13) 2,3,4,5, or 6 mercapto-C$_{1-3}$ alkyl,
(14) 5 C$_{1-3}$ alkylthio-C$_{1-3}$ alkyl,
(15) 4 or 5 hydroxy-C$_{1-3}$ alkyl,
(16) 4 or 5 C$_{1-3}$ alkoxy-C$_{1-3}$ alkyl,
(17) 4 or 5 amino-C$_{1-3}$ alkyl,
(18) 4 or 5 di(C$_{1-3}$ alkyl)amino-C$_{1-3}$ alkyl,
(19) 5 carboxy-C$_{1-3}$ alkyl,
(20) 4 or 5

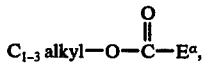, wherein E$^a$ is as defined above,
(21) when one R is hydroxy and another R is hydroxymethyl or mercaptomethyl on an adjacent carbon, the oxygens or oxygen and sulfur thereof may be joined together through a group of formula

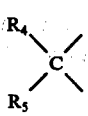

wherin R$_4$ and R$_5$ are the same or different and each is hydrogen, C$_{1-6}$ alkyl, or phenyl, or taken together, R$_4$ and R$_5$ represent =O or =S; with the proviso that if R$_1$ and R$_2$ are both hydrogen, and R$_3$$^a$ is hydrogen, —SO$_3$H, or

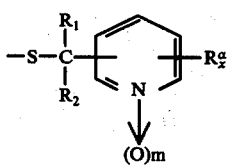

a. X is not zero;
b. R$^a$ is not —CH$_2$OH or —CH$_2$SH if X is 1;
c. if X is 1–4, then at least one R$^a$ group is other than C$_{1-5}$ alkyl or hydroxy;
d. if X is 3, one R$^a$ group is —CH$_3$, and another R$^a$ group is —OH, or C$_{2-6}$ alkanoyl, then the third R$^a$ group is other than —CH$_2$OH, —CH$_2$O(C$_{2-6}$ alkanoyl), CH=NOH, —CHO, —CH$_2$NH$_2$, —CH$_2$N(C$_{1-3}$ alkyl)$_2$ and the 3 and 4 R$^a$ groups together are not

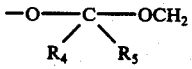

where $R_4$ and $R_5$ represent hydrogen or $C_{1-6}$ lower alkyl or phenyl.

A preferred embodiment of the novel compounds of this invention is the compound of structural formula:

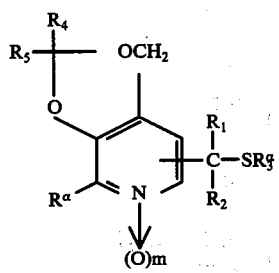

or pharmaceutically acceptable salt thereof, wherein $R^a$ is $C_{1-5}$ alkyl; $R_1$ is hydrogen, $C_{1-3}$ alkyl, or phenyl; $R_2$ is hydrogen or $C_{1-3}$ alkyl; $m$ is 0 or 1; $R_3{}^a$ is hydrogen or

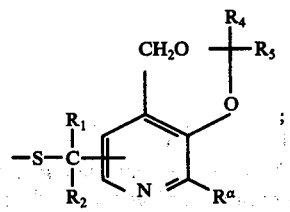

and $R_4$ and $R_5$ are the same or different and each is hydrogen, $C_{1-6}$ alkyl or phenyl, or taken together, $R_4$ and $R_5$ represent =O or =S, with the proviso that if $R_4$ and $R_5$ are hydrogen, $C_{1-6}$ alkyl or phenyl, then $m$ is 1.

Of particular interest are the compounds of structural formula

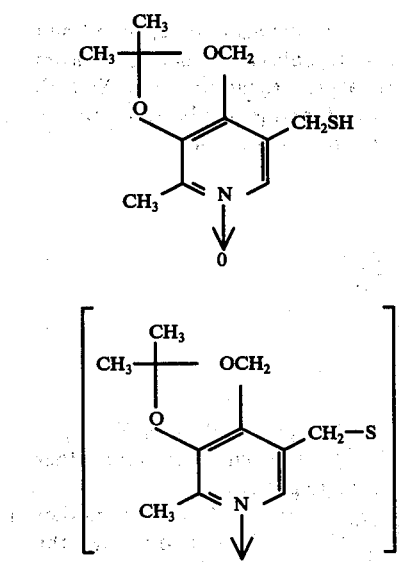

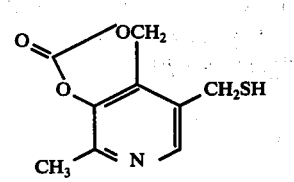

or pharmaceutically acceptable salts thereof.

Another preferred embodiment of the novel compounds is the compound of structure:

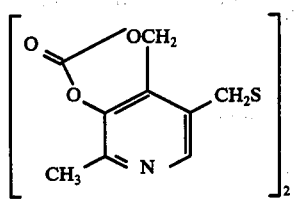

or pharmaceutically acceptable salt thereof, wherein $R_1$ is hydrogen, $C_{1-3}$ alkyl, or phenyl; $R_2$ is hydrogen or $C_{1-3}$ alkyl; $m$ is 0 or 1, $x$ is 3, and $R^a$ is $C_{1-5}$ alkyl, 3 or 5

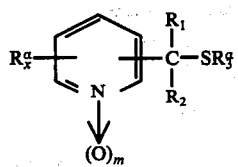

or 4 or 5

and $R_3$ is

or

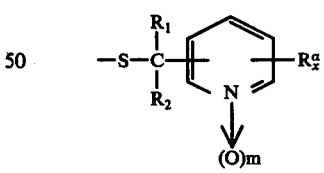

Of particular interest are the compounds wherein $E^a$ is $-O(C_{1-4}$ alkyl) and $NH_2$, and especially those of structure:

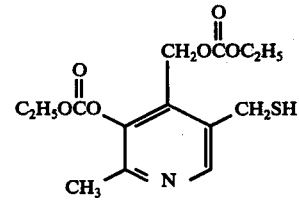

-continued

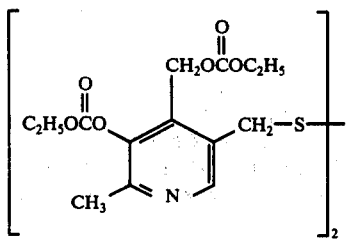

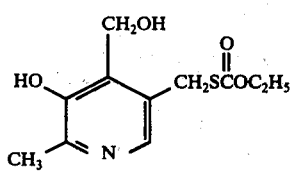

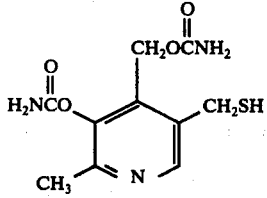

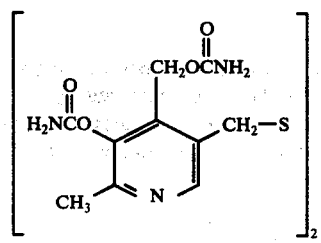

Another preferred embodiment of the novel compounds of this invention is the compound of structural formula:

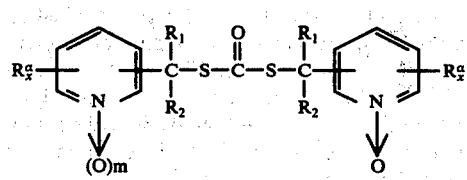

or pharmaceutically acceptable salt thereof, wherein $R_1$ is hydrogen, $C_{1-3}$ alkyl, or phenyl; $R_2$ is hydrogen or $C_{1-3}$ alkyl; m is 0 or 1; x is an integer from 0 –4, and $R^\alpha$ is (1) 3 or 5 hydroxy,
(2) 3, 5, or 6 $C_{1-3}$ alkoxy,
(3) 3 or 5

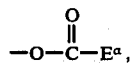

where $E^\alpha$ is as defined above,
(4) 5 carboxy,
(5) 5 carbamyl,
(6) 4 hydroximinomethyl,
(7) 4 formyl,
(8) 2, 3, 4, 5, or 6 $C_{1-5}$ alkyl,

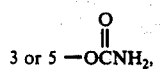

-continued

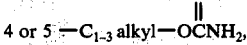

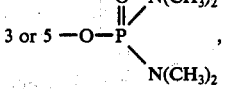

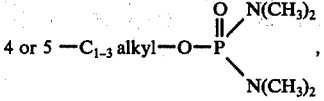

(13) 2, 3, 4, 5, or 6 mercapto-$C_{1-3}$ alkyl,
(14) 5 $C_{1-3}$ alkylthio-$C_{1-3}$ alkyl,
(15) 4 or 5 hydroxy-$C_{1-3}$ alkyl,
(16) 4 or 5 $C_{1-3}$ alkoxy-$C_{1-3}$ alkyl,
(17) 4 or 5 amino-$C_{1-3}$ alkyl,
(18) 4 or 5 di($C_{1-3}$ alkyl)amino-$C_{1-3}$ alkyl,
(19) 5 carboxy-$C_{1-3}$ alkyl,
(20) 4 or 5

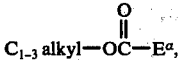

wherein $E^\alpha$ is as defined above.
(21) when one R is hydroxy and another R is hydroxymethyl or mercaptomethyl on an adjacent carbon, the oxygens or oxygen and sulfur thereof may be joined together through a group of formula:

wherein $R_4$ and $R_5$ are the same or different and each is hydrogen, $C_{1-6}$ alkyl, or phenyl, or taken together, $R_4$ and $R_5$ represent =O or =S; with the proviso that if $R_1$ and $R_2$ are both hydrogen, and $R_3{}^\alpha$ is hydrogen, —$SO_3H$, or

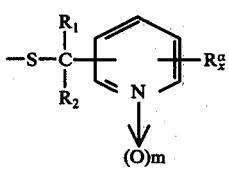

a. X is not zero;
b. $R^\alpha$ is not —$CH_2OH$ or —$CH_2SH$ if x is 1;
c. if x is 1–4, then at least one $R^\alpha$ group is other than $C_{1-5}$ alkyl or hydroxy;
d. if x is 3, one $R^\alpha$ group is —$CH_3$, and another R group is —OH, or $C_{2-6}$ alkanoyl, then the third R group is other than —$CH_2OH$, —$CH_2O(C_{2-6}$ alkanoy CH=NOH, —CHO, —$CH_2NH_2$, —$CH_2N(C_1$ alkyl$)_2$ and the 3 and 4 $R^\alpha$ groups together are not

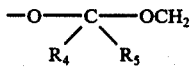

where $R_4$ and $R_5$ represent hydrogen or $C_{1-6}$ lower alkyl or phenyl.

Of particular interest is the compound of structure:

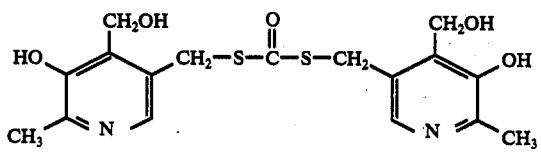

Another preferred embodiment of the novel compounds of this invention is the compound of formula:

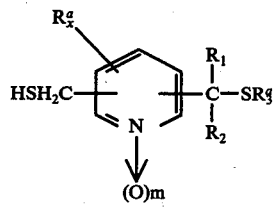

or pharmaceutically acceptable salts thereof wherein
R$_1$ is hydrogen, C$_{1-3}$ alkyl or phenyl;
R$_2$ is hydrogen or C$_{1-3}$ alkyl;
R$_3{}^a$ is hydrogen, —SO$_3$H, —PO$_3$H$_2$,

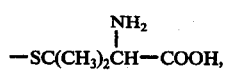

adamantanoyl, benzoyl, C$_{3-8}$ cycloalkylcarbonyl, C$_{1-5}$ alkoxycarbonyl, or

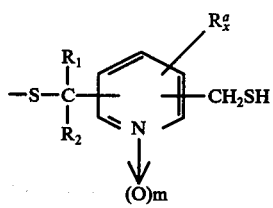

m is 0 or 1;
x is an integer from 0–3; and
R is
(1) 3 or 5 hydroxy,
(2) 3, 5, or 6 C$_{1-3}$ alkoxy,
(3) 5 carboxy,
(4) 4 formyl,
(5) 4 hydroximinomethyl,
(6) 2, 3, 4, 5, or 6 C$_{1-5}$ alkyl,
(7) 5 C$_{1-3}$ alkylthio-C$_{1-3}$ alkyl,
(8) 4 or 5 C$_{1-3}$ alkoxy-C$_{1-3}$ alkyl,
(9) 4 or 5 amino-C$_{1-3}$ alkyl,
(10) 4 or 5 di(C$_{1-3}$ alkyl)amino-C$_{1-3}$ alkyl,
(11) 5 carboxy-C$_{1-3}$ alkyl, with the proviso that when R$_1$ and R$_2$ are both hydrogen then X is not zero, and when X is 2 and R represents 2-methyl and 3-hydroxy, then the —CH$_2$SH and

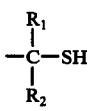

are not in the 4 and 5 positions.

Of particular interest are the novel compounds described immediately above wherein the —CH$_2$SH and

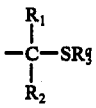

are alternatively in the 2 and 4 positions.

The disulfide dimers and mixed disulfides referred to above, have the respective general structural formulae:

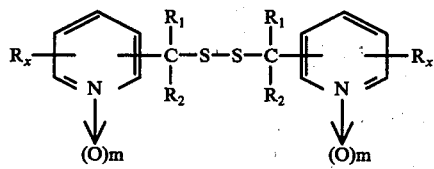

and

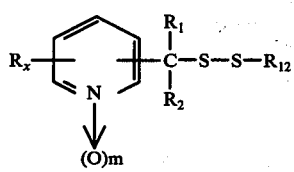

In the above descriptions R$_3$ has been defined in part as —SO$_3$H and —PO$_3$H$_2$ to facilitate description. It is understood that molecules within these descriptions actually exist as internal salts, having structures such as

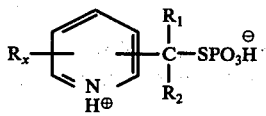

The Bunte salts as well as having utility against rheumatoid arthritis, are valuable intermediates in the synthesis of the disulfides. Thus, these Bunte salts form another embodiment of this invention.

Certain of the other compounds described above can and do exist as isomers and cyclic internal condensation products, for example:

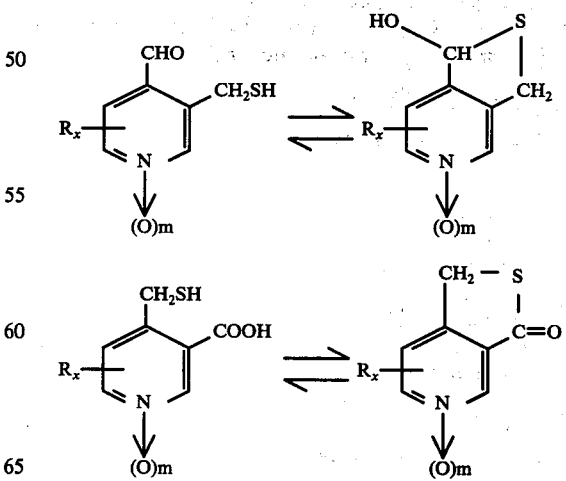

The pharmaceutically acceptable addition salts include those prepared from mineral and organic acids commonly employed in the pharmaceutical art, such as hydrochloric, hydrobromic, sulfuric, nitric, maleic, fumaric, tartaric, or succinic acids. Other salts included herein are alkali metal salts of the mercaptan group and divalent metal complexes of the mercapto group with such as calcium or magnesium.

It is well known in the art that the mercapto group is subject to reaction with aldehydes and ketones to form hemimercaptals and hemimercaptoles. It is similarly known in the art, Field et al., J. Med. Chem., 12, 624-628 (1969), that many of these hemimercaptals and hemimercaptoles prepared from biologically active mercaptans serve as "latentiating" derivatives, or as chemical modifications of biologically active compounds to form new compounds, which upon in vivo enzymatic or chemical transformation will liberate the parent compounds. Latentiation may also provide means of favorably influencing absorption, transport, distribution, localization, metabolism, and toxicity, duration of action, as well as stability. Included within the group of aldehydes and ketones suitable for this purpose are chloral, hexafluoro-acetone, acetone, benzaldehyde, pyruvate or ketomalonate. Since latentiation of mercapto groups by this means is known in the art, these latentiating derivatives are considered to be within the spirit and scope of the novel method of treatment and novel compounds of this invention.

Another means of latentiation is by addition of the thiols of this invention to $\alpha$, $\beta$-unsaturated acids such as maleic acid and cinnamic acid as described by Srivistava et al., in J. Med. Chem., 16, 428-429 (1973).

Latentiation may also be achieved by substitution of the mercapto hydrogen with a 1-methyl-4-nitroimidazol-5-yl group as in azathioprine.

It is also well known in the art that pivaloyloxymethyl derivatives provide a pharmacologically attractive form of pharmaceutical agent and such derivatives are also included within the scope of this invention.

In spite of the extensive antiinflammatory research in the past two decades, there is still an obvious need for an effective and well tolerated agent for the treatment of rheumatoid arthritis. Conventional nonsteroidal, antiinflammatory-analgesic-antipyretic agents, such as aspirin, and many experimental new drugs under clinical evaluation, are effective in providing symptomatic relief of the acute syndrome only but are unable to alter the course of the disease. As a consequence, the antirheumatic actions of two old remedies, gold and D-penicillamine, in spite of their potential side effects, have received renewed interest in the past few years. The clinical efficacy of both drugs was reconfirmed by well-controlled multi-center clinical studies. Several rheumatologists have expressed the opinion that a superior D-penicillamine-like compound would be a valuable contribution to medicine in this important field. It is, therefore, an important discovery that many of the known mercaptomethyl pyridines and the novel mercaptomethyl pyridines of this invention have an important degree of anti-rheumatoid arthritis activity.

For these purposes the compounds of the invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection, intraarticular, or infusion techniques. In addition to the treatment of warm-blooded animals such as mice, rats, horses, dogs, cats, guinea pigs, rabbits, etc., the compounds of the invention are effective in the treatment of humans.

The pharmaceutical compositions containing the active ingredient may be in a form suitable for oral use, for example, as tablets, troches, lozenges, aqeuous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweeting agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegatable oil, for example olive oil or arachis oils, or a mineral oil, for example liquid paraffin or mixtures of these. Suitable emulsifying agents may be naturally-occurring gums, for example gum acacia or gum tragacanth, naturally-occuring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the antiinflammatory agents are employed.

Dosage levels of the order of 1 mg. to 140 mg. per kilogram of body weight per day are useful in the treatment of the above-indicated conditions. Generally, an effective dosage range is 5–50 mg. per kilogram of body weight per day.

The amount of active ingredient that may be combined with the carrier materials to produce a single dosage form will vary depending upon the host treated and the particular mode of administration. For example, a formulation intended for the oral administration of humans may contain from 5 mg. to 5 gm. of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The mercaptoalkylpyridines of this invention are generally prepared from the corresponding hydroxyalkyl, haloalkyl, methanesulfonyloxyalkyl, benzenesulfonyloxyalkyl, or toluenesulfonyloxyalkyl compounds.

Where the mercaptoalkyl group occurs in the 2, 4, or 6 position of the pyridine ring and is adjacent to an hydroxyl group, it is readily formed by dissolving the hydroxymethyl compound in a lower alkanol, preferably ethanol, containing an alkali metal hydroxide, such as sodium hydroxide or potassium hydroxide, treating the solution with carbon disulfide and heating for 2–8 hours at a temperature from 50° C. to reflux, followed by acidification of the cooled mixture. Isolation is accomplished by standard techniques such as concentration to dryness and extraction with a solvent.

The mercaptoalkyl group in any position, but particularly in the 3 or 5 position of the pyridine ring is frequently prepared by first converting the corresponding hydroxymethyl group to the chloromethyl or bromomethyl by heating at 50° C. to reflux temperature for 1–4 hours with thionyl chloride or with concentrated hydrobromic acid respectively.

The sulfonyloxy compounds are prepared by esterification of the corresponding hydroxyalkyl compounds by standard procedures. Hydrobromic acid may not be used in the presence of acid labile groups. The resulting haloalkyl or sulfonyloxy compound is then treated in various alternate procedures.

A. The halo or sulfonyloxy compound in aqueous solution is treated with ethyl potassium xanthogenate at 5°–10° C. for 1–4 days, and the xanthate product is extracted out with a solvent such as ether and reduced with lithium aluminum hydride, lithium borohydride, sodium borohydride, or the like. Alternatively, the xanthate can be converted to mercapto by heating at 50° C. to reflux with aqueous or alcoholic alkali such as sodium or potassium hydroxide.

B. The halomethyl compound is heated in a lower alkanol such as methanol, with thiourea at 50° C. to reflux for 1–4 hours. The thioureide is then heated at 50° C. to reflux in water or lower alkanol such as ethanol containing an alkali metal hydroxide such as sodium or potassium hydroxide.

C. The halo or sulfonyloxy compound is converted to a Bunte salt by treatment with sodium thiosulfate in aqueous alcohol at 50°–100° C. for a few minutes to about 2 hours. Treatment of the Bunte salt with dilute acid, usually sulfuric acid in the absence of air, at 25° C. to reflux temperature for 1–6 hours produced the mercaptoalkyl group.

D. The halo or sulfonyloxy compound is treated with trisodium phosphorothioate in aqueous solution at about 0°–10° C. for 10–20 hours to produce the phosphorothioate compound. Treatment of this product with an alkali metal hydroxide at 50°–100° C. for a few minutes to about 2 hours produces the mercaptoalkyl compound.

E. The halo or sulfonyloxy compound on treatment with an alkali metal hydrosulfide at about room temperature for 10-24 hours in an anhydrous alcohol, DMF, or the like, produces the mercaptoalkyl compounds directly.

F. Treatment of a halo or sulfonyloxy compound with disodium trithiocarbonate in aqueous alkanol at 25°-100° C. for 1-6 hours in the absence of air, followed by adjustment to approximate neutrality produces the sodium trithiocarbonate alkylpyridine which, on treatment with dilute acid such as 1N hydrochloric acid at 20°-50° C., for a few minutes to 4 hours under nitrogen, provides the mercaptoalkyl compound.

Alternatively, sodium trithiocarbonate at 20°-30° C. in a lower alkanol without pH adjustment provides a bis(pyridylmethyl)trithiocarbonate, which on alkaline hydrolysis in the absence of air, provides the mercaptoalkyl compound.

C. The halo or sulfonyloxy compounds are converted to bis[pyridylalkyl]disulfides by procedures to be discussed later. These disulfides are reduced to mercaptoalkylpyridines by various procedures such as: (1) catalytic hydrogenation with catalysts such as palladium on carbon in inert solvent such as an alkanol at approximately room temperature; (2) with reducing agents such as sodium borohydride, lithium aluminum hydride, lithium borohydride or the like in an anhydrous solvent such as tetrahydrofuran, at 0°-25° C.; (3) with zinc and an acid such as acetic or hydrochloric acid at 50° to 100° C. for 1-6 hours; (4) by treatment with a mercaptan such as ethyl mercaptan at 20°-50° C. for 10-24 hours; (5) electrolysis of an aqueous solution between a mercury cathode and platinum anode at 10-30 milliamps and 25-50 volts.

The halo or sulfonyloxy compounds can be converted to the disulfides by treatment with disodium disulfide in an aqueous alkanol at room temperature to about 50° C. for 1-6 hours.

Alternatively, the Bunte salts of this invention are converted to symmetrical disulfides by various procedures such as:

A. Heating at 50°-100° C. with dilute aqueous mineral acid such as 1N sulfuric acid for 10-24 hours.

B. Treating it at 20°-50° C. in an aqueous alkanol with aqueous $Na_2S$ or $Na_2S_2$ solution which causes precipitation of the disulfide.

C. Treating it at 20-50° C. in an aqueous alkanol with an alkanolic solution of iodine for 1 to 3 days.

D. Heating it at 50°-100° C. in dilute aqueous alkali metal hydroxide, either alone or with the corresponding mercaptoalkyl compound for 1 to 4 hours.

Another method of preparing the disulfides of this invention is by treating an ethyl xanthate with aqueous or aqueous alkanolic ammonium hydroxide for 1-4 days at ambient temperature or with ammonium hydroxide and hydrogen peroxide for 1-3 hours.

The isothioureides are also readily converted to disulfides by treatment with aqueous sodium tetrathionate and an alkali metal hydroxide for 15 minutes to 2 hours at ambient temperature. The disulfides are also prepared from isothioureides by treatment with hydrogen peroxide in an alkanolic solution over a period of 2-6 days at ambient temperature.

The sodium trithiocarbonates or bis(pyridylmethyl)-trithiocarbonates are convertible to the disulfides of this invention by refluxing an aqueous mixture for 10-24 hours.

The mercaptoalkyl compounds of this invention are also convertible to the disulfides by oxidation with hydrogen peroxide at 0°-10° C. in dilute acid solution; by bubbling air or oxygen through a solution of the mercaptan in an organic solvent for 10-24 hours at room temperature; by treatment with a per acid such as per acetic, m-chloroperbenzoic, or perphthalic acid; or by treatment with iodine in aqueous alcohol.

The Bunte salts, as well as being useful in the novel method of treatment, find utility as an intermediate in the preparation of disulfides, both symmetrical and unsymmetrical. The mixed disulfides are obtained by heating at 50°-100° C. a mixture of molar equivalents of a Bunte salt, and a mercapto compound with aqueous sodium or potassium hydroxide.

Another type of derivative found useful both as a final product and as particularly useful protective groups because they tie up both an hydroxyl group and a vicinal hydroxymethyl or mercaptomethyl, are the cyclic ketals and acetals. They are prepared by treating, for example, a 3-hydroxy-4-hydroxymethyl compound with a carbonyl compound such as acetone or benzaldehyde saturated with hydrogen chloride at −5° C. to +5° C. for 2-6 hours.

A typical derivative is:

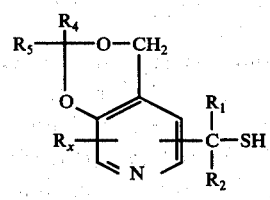

These groups are readily removed by warming at 50°-100° C., for 10-60 minutes, in dilute aqueous acid to regenerate the two hydroxy groups.

Where the desired product is in the form of its N-oxide, the oxygen must be introduced before the mercapto group, as the latter is subject to oxidation. They are usually prepared by treating a pyridine free base with a peracid such as m-chloroperbenzoic acid at room temperature in an inert solvent such as chloroform, or methylene chloride for a period of 16-48 hours.

Carbonyl derivatives of a nuclear hydroxy, a hydroxyalkyl, and/or a mercaptoalkyl group such as carbonates, esters and carbamoyl derivates are prepared generally by treating the hydroxy or mercapto compound in an inert solvent such as tetrahydrofuran, preferably in the presence of an acid acceptor such as an organic base such as pyridine or in the organic base alone as solvent with an alkyl chloroformate, alkanoyl halide or anhydride, or a carbamoyl halide respectively at room temperature to reflux temperature for 1 hour to 2 days. Selective derivatization is obtained by the use of blocking groups, and/or chromatographic separation of the products.

Related carbonyl derivatives are those prepared from dicarbonyl compounds such as isophthaloyl chloride, oxalyl chloride, glutareyl chloride piperazine-1,4-dicarbonyl chloride or the like, and two equivalents of a mercaptoalkylpyridine of this invention by the above described procedure to a compound of partial structure $$-S-\underset{\underset{O}{\|}}{C}-(L)_{0-1}-\underset{\underset{O}{\|}}{C}-S-,$$

where L is as previously defined.

Similarly, phosgene provides the compound of partial structure $$-S-\underset{\underset{O}{\|}}{C}-S-.$$

Under similar conditions with a suitably protected mercaptoalkyl group, phosgene provides a cyclic carbonate derivative of partial structure:

[structure shown]

—S— Carbamates may be prepared by treating a mercaptoalkyl compound with phosgene in an inert aromatic solvent such as benzene, followed by treatment with an amine or ammonia.

Related to the previously mentioned disulfides are the tri- and tetrasulfides. These are prepared by treatment of a mercaptoalkyl pyridine in an inert solvent such as DMF or DMSO, with sodium hydride or metal organic at 0°–10° C. followed by treatment with sulfur dichloride or sulfur monochloride for 5–24 hours.

The intermediate compounds convertible by the previously described methods to the mercaptoalkyl compounds useful in this invention carry in the 2-position, hydrogen, alkyl or hydroxy alkyl. These are all available from known starting materials.

The 3-position is usually hydroxy, which is available on known starting materials, or functional derivatives thereof. The methyl ether is prepared by treatment with diazomethane in ether. Other ethers are prepared by the usual methods of treating the hydroxy compound with an alkali metal hydroxide and an alkyl halide in a refluxing lower alkanol.

A 4-alkyl group is prepared by first preparing the 4-tosyloxyalkyl group by treatment of the 4-hydroxyalkyl compound with toluenesulfonyl chloride in pyridine at room temperature to about 100° C. for 1 hour to about 2 days, followed by reduction with lithium aluminum hydride in the usual way.

The 5-carboxy pyridines are known and are convertible to a 5-carbamyl analog by treatment of an ester, lactone, or thiolactone with concentrated ammonia.

5-Carboxyalkyl compounds are prepared from 5-haloalkyl analog by treatment with sodium cyanide, followed by alkaline hydrolysis of the resulting nitrile.

Of particular interest in this invention are the compounds of formula:

[Structure I: pyridine N-oxide with CH₂SH group]

and

[Structure II: disulfide dimer]

Compound I is prepared from a compound of formula:

[Structure III: pyridine N-oxide with CH₂S—A group]

wherein A is $-\underset{NH_2}{\overset{NH}{C\diagup\kern-1em\diagdown}}$ , $PO_3H_2$, $-\underset{\underset{}{\overset{S}{\|}}}{C}-O(C_{1-4}\text{ alkyl})$ or

[structure: pyridine N-oxide with SCH₂ and CH₂O— groups]

by a process which comprises heating Compound III, where A is $$-C\underset{NH_2}{\overset{NH}{\diagup\kern-1em\diagdown}}$$

or $PO_3H_2$ at 50°–100° C. in dilute aqueous alkali metal hydroxide for 10 minutes to 2 hours.

Alternatively, the disulfide, or the compound wherein A is $$-\underset{\underset{}{\overset{S}{\|}}}{C}-O(C_{1-4}\text{ alkyl}),$$

is reduced with lithium borohydride, lithium aluminum hydride, sodium borohydride, or the like in an anhydrous aprotic solvent such as THF, ether, glyme, diglyme, or the like at 0°–25° C.

Alternatively, the disulfide is reduced catalytically with hydrogen in the presence of a noble metal catalyst such as palladium on carbon, platinum, or the like, preferably at room temperature until the theoretical amount of hydrogen is absorbed.

Compound II is prepared from a compound of structure:

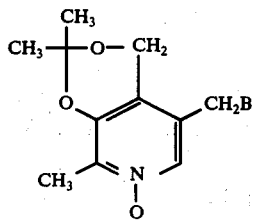

wherein B is halo, $-OSO_2CH_3$, $-OSO_2C_6H_5$, $-OSO_2C_6H_4CH_3$,

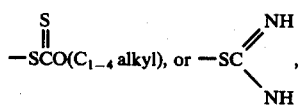

by the processes previously described for the preparation of disulfides.

Another compound of interest in this invention is of structure:

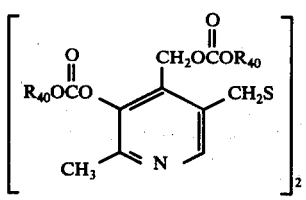

where $R_{40}$ is $C_{1-5}$ alkyl or $C_{2-5}$ alkenyl.

It is prepared by:

a. acylation of bonifen with $R_{40}$ chloroformate as previously described;

b. treatment of bonifen with the $R_{40}$ ester of 1-chloro-N-phenyl formamidic acid, followed by hydrolysis of the phenylimino group with mineral acid such as 6N hydrochloric at 20°–50° C. for 1–5 hours. Other N-substituted formamidic acids, such as N-$C_{1-5}$ alkyl, N-benzyl, or the like, may also be used;

c. treatment of bonifen in an anhydrous solvent such as DMF with at least 4 equivalents of sodium hydride and $R_{40}$ 2,2,2-trichloroethyl carbonate at 20°–50° C. for 10–20 hours;

d. by oxidation of 2-methyl-3-$R_{40}$O-carbonyloxy-4-$R_{40}$O-carbonyloxymethyl-5-mercaptomethylpyridine with hydrogen peroxide, air, oxygen, per acid or iodine as previously described for preparation of disulfides from mercaptans;

e. by treatment of 2-methyl-3-$R_{40}$O-carbonyloxy-4-$R_{40}$O-carbonyloxymethylpyridyl-5-methylthiosulfuric acid with a mineral acid or iodine as previously described for conversion of Bunte salts to disulfides;

f. treatment of 2-methyl-3-$R_{40}$O-carbonyloxy-4-$R_{40}$O-carbonyloxymethylpyridyl-5-methylisothioureide with hydrogen peroxide in an alkanol for 2–4 days at room temperature.

Another compound of interest is of structure:

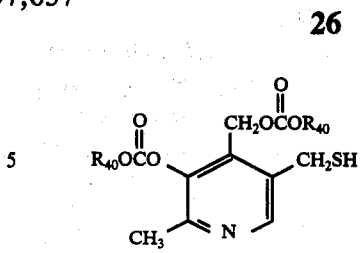

It is prepared by:

a. reduction of Compound IV with Zn/acid, $NaBH_4$, $LiAlH_4$, or $LiBH_4$, mercaptan, catalytically or electrolytically as previously described for conversion of disulfides to mercaptans;

b. treatment of 2-methyl-3-$R_{40}$O-carbonyloxy-4-$R_{40}$O-carbonyloxymethyl-5-chloromethylpyridine with an alkali metal hydrosulfide as previously described;

c. treatment of 2-methyl-3-$R_{40}$O-carbonyloxy-4-$R_{40}$O-carbonyloxymethylpyridyl-5-thiosulfuric acid with sulfuric acid in the absence of air as previously described;

d. reduction of ethyl 2-methyl-3-$R_{40}$O-carbonyloxy-4-$R_{40}$O-carbonyloxymethylpyridyl-5-methylxanthogenate with $LiAlH_4$, $NaBH_4$, or $LiBH_4$ as previously described;

e. treatment of sodium (3-$R_{40}$O-carbonyloxy-4-$R_{40}$O-carbonyloxymethyl-2-methylpyridyl-5-methyl) trithiocarbonate with dilute mineral acid in the absence of air for 0.5–3 hours at 20°–50° C.

Another compound of interest in this invention is of formula:

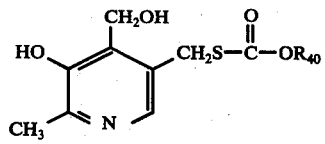

It is prepared by:

a. alkylation of Bender's salt

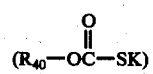

or other alkali metal analog with 2-methyl-3-hydroxy-4-hydroxymethyl-5-mercaptomethylpyridine in an aqueous alkanol at 0°–20° C. for 2 to 10 hours;

b. hydrolysis of a compound of formula:

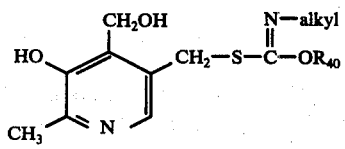

with dilute mineral acid at ambient temperature for 2–10 hours;

c. hydrolysis of a compound of formula:

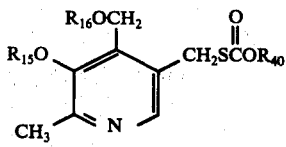

with aqueous mineral acid at 0°–25° C. for ¼ to 4 hours, wherein R$_{15}$ and R$_{16}$ are the same or different and represent acid labile protecting groups such as tetrahydropyranyl or R$_{15}$ and R$_{16}$ taken together represent a group of formula

wherein R$_4$ and R$_5$ are the same or different and represent hydrogen, C$_{1-3}$ alkyl, or phenyl.

Another compound of interest in this invention is of formula:

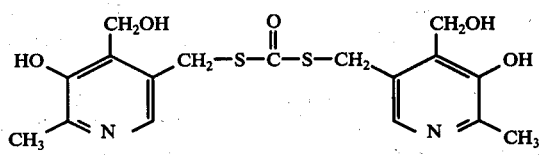

It is prepared by:

a. treatment of 2-methyl-3-hydroxy-1-hydroxymethyl-5-mercaptomethylpyridine with p-nitrophenylchloroformate in an aprotic solvent such as THF, ether, glyme, diglyme or the like at 0°–10° C. for 1–3 hours followed by warming to 20°–50° C;

b. hydrolysis of a compound of formula:

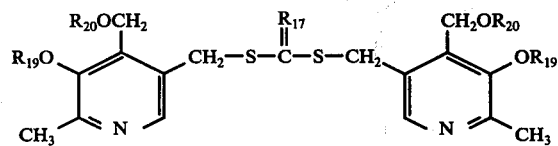

with dilute mineral acid at 20°–50° C. for 1–5 hours, where R$_{19}$ and R$_{20}$ are the same or different and represent hydrogen, an acid labile protecting group such as tetrahydropyranyl or R$_{19}$ and R$_{20}$ together represent a group of formula:

where R$_4$ and R$_5$ are the same or different and represent hydrogen, C$_{1-3}$ alkyl, or phenyl; and R$_{17}$ represents =O or =N—R$_{18}$, where R$_{18}$ represents hydrogen, phenyl, or C$_{1-3}$ alkyl, with the provisio that where R$_{17}$ is =O, then R$_{19}$ and R$_{20}$ are not both hydrogen;

c. oxidation of a compound of formula:

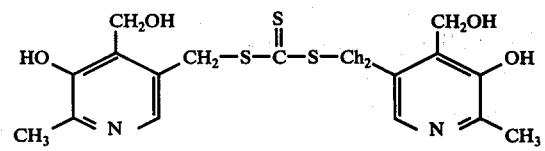

with an oxidizing agent such as potassium permanganate, nitric acid, mercuric oxide, or the like at ambient temperature for 1–3 hours;

d. acid hydrolysis of a compound of formula:

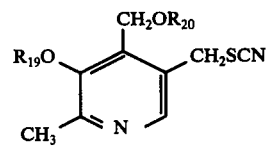

with mineral acid and slow warming to about 80°–100° C., where R$_{19}$ and R$_{20}$ are as previously described.

Another compound of importance in this invention is of structure:

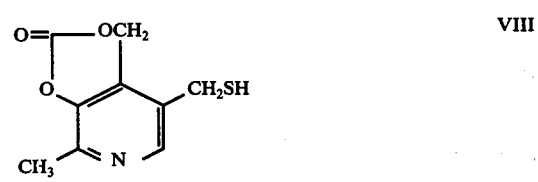

It is prepared by:

a. reduction of Compound IX with Zn/acid, NaBH$_4$, LiAlH$_4$, or LiBH$_4$, mercaptan, catalytically or electrolytically as previously described for conversion of disulfides or mercaptans;

b. treatment of 5-chloromethyl-8-methyl-2-oxo-4H-m-dioxino[4,5-c]pyridine with an alkali metal hydrosulfide as previously described;

c. treatment of 8-methyl-2-oxo-4H-m-dioxino[4,5-c]-pyridine-5-thiosulfuric acid with sulfuric acid in the absence of air as previously described;

d. reduction of C$_{1-4}$ alkyl 8-methyl-2-oxo-4H-m-dioxino[4,5-c]pyridine-5-methylxanthogenate with LiAlH$_4$, NaBH$_4$, or LiBH$_4$ as previously described;

c. treatment of an alkali metal (8-methyl-2-oxo-4H-m-dioxino[4,5-c]pyridine-5-methyl)trithiocarbonate with dilute mineral acid in the absence of air for 0.5–3 hours at 20°–50° C.

Another compound of importance in this invention is of structure:

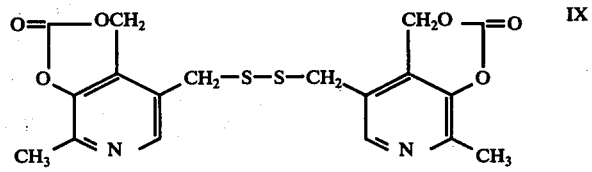

It is prepared by:

a. acylation of bonifen with 2 equivalents phosgene at 0°–10° C., followed by aging at room temperature to 50° C. for 3–24 hours in an inert solvent or mixtures of solvents such as chloroform, benzene, pyridine or the like;

b. acid hydrolysis of a compound of formula:

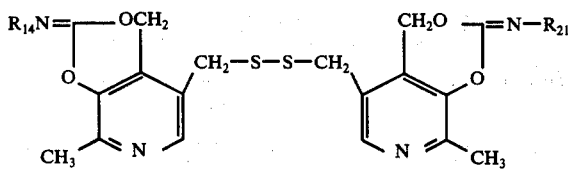

where $R_{21}$ is phenyl, benzyl, or $C_{1-5}$ alkyl with a dilute mineral acid at room temperature to 100° C. for 1–16 hours;

c. treatment of bonifen with $C_{1-4}$ alkyl carbonate in the presence of a strong base such as an alkali metal alkoxide at reflux temperature with downward distillation of the liberated alkanol until reaction is complete;

d. oxidation of Compound VIII with hydrogen peroxide, air, oxygen, per acid or iodine as previously described for preparation of disulfides from mercaptans;

e. treatment of 8-methyl-2-oxo-4H-m-dioxino[4,5-c]-pyridine-5-thiosulfuric acid with a mineral acid or iodine as previously described for conversion of Bunte salts to disulfides.

Another compound of interest in this invention is of structure:

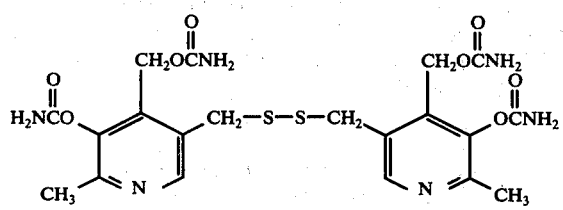

It is prepared by:

a. bonifen is treated with an excess of urea and manganous acetate at 135°–155° C. for 2–6 hours;

b. bonifen is treated with with an excess of phosgene at 0°–10° C. in an inert organic solvent followed by removal of the excess phosgene and treatment with ammonia at 0° C. to room temperature;

c. bonifen is treated with an excess of an alkali metal cyanate and trifluoroacetic acid in an inert organic solvent at 20°–80° C. for 2–10 hours;

d. bonifen is treated with an excess of an alkyl carbamate and aluminum isopropoxide in toluene at reflux temperature with downward distillation of the alkanol-toluene azeotrope until the reaction is complete;

e. bonifen is treated with carbamoyl chloride in an organic solvent in the presence of an acid acceptor such as pyridine at 0°–50° C. for 5–24 hours;

f. Compound XI is oxidized with hydrogen peroxide, air, oxygen, per acids or iodine as previously described for preparation of disulfides from mercaptans;

g. by treatment of 2-methyl-3-carbamyloxy-4-carbamyloxymethylpyridine-5-thiosulfuric acid with sulfuric acid or iodine as previously described for conversion of Bunte salts to disulfides;

h. by treatment of 2-methyl-3-carbamyloxy-4-carbamyloxymethyl-5-isothioureidomethylpyridine with hydrogen peroxide at 20°–50° C. for 2–6 days.

Another compound of interest in this invention is of structure:

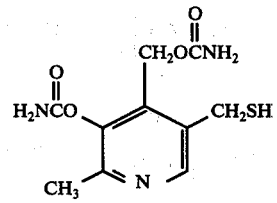

It is prepared by:

a. reduction of Compound X as previously described for reduction of disulfides to mercaptans;

b. treatment of 2-methyl-3-carbamyloxy-4-carbamyloxymethyl-5-chloromethylpyridine with alkali metal hydrosulfide as previously described;

c. treatment of 2-methyl-3-carbamyloxy-4-carbamyloxymethylpyridyl-5-methylthiosulfuric acid with mineral acid in the absence of air as previously described;

d. reduction of $C_{1-4}$ alkyl 2-methyl-3-carbamyloxy-4-carbamyloxymethylpyridine-5-methyl xanthogenate with $LiAlH_4$, $NaBH_4$, or $LiBH_4$ as previously described;

e. treatment of an alkali metal (2-methyl-3-carbamyloxy-4-carbamyloxymethylpyridyl-5-methyl)trithiocarbonate with dilute mineral acid in the absence of air for 0.5–3 hours at 20°–50° C.

Another compound of interest in this invention is of formula:

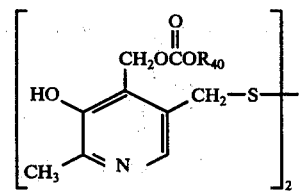

and is prepared by oxidation of the corresponding mercaptan with hydrogen peroxide, air, oxygen, or per acids as previously described. Alternatively, it is prepared by a Diels Alder reaction between the following reagents:

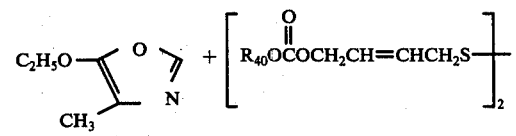

EXAMPLE 1

2-Methyl-3-Hydroxy-4-Mercaptomethyl-5-(2-hydroxyethyl) Pyridine Hydrochloride

To a solution of 3.0 g. of sodium hydroxide in 125 ml. of ethanol was added 2.4 g. of 5-homopyridoxine hydrochloride in 50 ml. of ethanol. After stirring 10 minutes, 5 ml. of carbon disulfide was added, and the mixture was refluxed 4 hours. The cooled mixture was acidified with hydrochloric acid and concentrated to dryness. The residue was extracted with 2 × 200 ml. of boiling ethanol, and the extract was concentrated to dryness. The oily residue was recrystallized by dissolving it in tetrahydrofuran and adding isopropanol dropwise to incipient cloudiness and aging to give 2-methyl-3-hydroxy-4-mercaptomethyl-5-(2-hydroxyethyl)pyridine hydrochloride, m.p. 119°–120° C.

Employing the procedure of Example 1, but substituting for the 5-homopyridoxine hydrochloride used therein an equivalent amount of each of 2-methyl-3-hydroxy-4-hydroxymethyl-5-methylthiomethylpyridine;
2-methyl-3-hydroxy-4-hydroxymethyl-5-hydroxymethyl-6-methylpyridine;
2-methyl-3-hydroxy-4-hydroxymethyl-5-aminomethylpyridine;
2-methyl-3-hydroxy-4-hydroxymethyl-5-hydroxymethylpyridine-N-oxide;
2-ethyl-3-hydroxy-4-hydroxymethyl-5-hydroxymethylpyridine;
2-methyl-3-hydroxy-4-hydroxymethylnicotinic acid lactone;
2-methyl-5-hydroxy-6-hydroxymethylpyridine; and
pyrithioxine;

there are produced respectively, 2-methyl-3-hydroxy-4-mercaptomethyl-5-methylthiomethylpyridine hydrochloride, (oil)
2-methyl-3-hydroxy-4-mercaptomethyl-5-hydroxymethyl-6-methylpyridine hydrochloride, m.p. 252°–253° C.;
2-methyl-3-hydroxy-4-mercaptomethyl-5-aminomethylpyridine dihydrochloride monohydrate, m.p. 146°–148° C.;
2-methyl-3-hydroxy-4-mercaptomethyl-5-hydroxymethylpyridine-N-oxide, m.p. 168°–170° C.;
2-ethyl-3-hydroxy-4-mercaptomethyl-5-hydroxymethylpyridine, m.p. 108°–112° C.; and
2-methyl-3-hydroxy-4-mercaptomethylpyridine-5-carboxylic acid thiolactone, m.p. 280°–285° C. (free base obtained by neutralizing aqueous solution of hydrochloride with sodium bicarbonate);
2-methyl-5-hydroxy-6-mercaptomethylpyridine hydrochloride, m.p. 192°–194° C.;
bis[2-methyl-3-hydroxy-4-mercaptomethyl-5-pyridylmethyl] disulfide, m.p. 178°–180° C. (dec.);

EXAMPLE 2

2-Methyl-3-Hydroxy-4-Mercaptomethylnicotinic Acid Amide

2-Methyl-3-hydroxy-4-mercaptomethylpyridine-5-carboxylic acid thiolactone (3.0 g.) was added to 50 ml. of liquid ammonia and refluxed for 5 hours. The ammonia was allowed to evaporate, and the residue was washed with ether and ethanol to give 2-methyl-3-hydroxy-4-mercaptomethylnicotinic acid amide, m.p. 300° dec.

EXAMPLE 3

3-Mercaptomethylpyridine-N-Oxide

Step A: Preparation of 3-chloromethylpyridine-N-oxide hydrochloride

A solution of 30 g. of 3-hydroxymethylpyridine-N-oxide in 200 ml. of benzene and 18.4 g. of thionyl chloride was refluxed 2 hours, cooled and filtered to give 3-mercaptomethylpyridine-N-oxide.

Step B: Preparation of 3-thioureidomethylpyridine-N-oxide dihydrochloride

The chloromethyl compound (34.2 g.) from Step A, in 200 ml. of methanol was refluxed with 17.3 g. of thiourea for 2 hours. The precipitate was collected and air dried to give 12.4 g. of 3-thioureidomethylpyridine-N-oxide dihydrochloride, m.p. 145°–148° C.

Step C: Preparation of 3-mercaptomethylpyridine-N-oxide

The thioureido compound (8 gm.) from Step B was refluxed in 50 ml. absolute ethanolic sodium hydroxide (6.5% w/v) for 4 hours under nitrogen, cooled and evaporated to dryness. The residue was dissolved in 50 ml. of water and 50 ml. of glacial acetic acid and evaporated to near dryness, and extracted with 4 × 40 ml. of chloroform. The chloroform was washed with 1 × 20 ml. of water, dried over magnesium sulfate, and treated with gaseous hydrogen chloride. The precipitate was collected, washed with acetone and dried to give 2.0 g. of 3-mercaptomethylpyridine-N-oxide hydrochloride, m.p. 184°–190° C.

EXAMPLE 4

Bis(2-Isobutyl-3-Hydroxy-4-Hydroxymethyl-5-Pyridylmethyl) Disulfide, Dihydrochloride Step A: Preparation of 2-isobutyl-3-hydroxy-4,5-di(bromomethyl)pyridine hydrobromide A solution of 3 g. of 2-isobutyl-3-hydroxy-4,5-di(hydroxymethyl)pyridine in 30 ml. of 48% hydrogen bromide was refluxed 20 minutes, cooled, and evaporated to an oil (7.4 g.).

Step B: Preparation of ethyl 2-isobutyl-3-hydroxy-4-hydroxymethyl-5-pyridylmethylxanthate A solution of the bromomethyl compound (7 g.) from Step A in 100 ml. of water was added to 35 g. of ethyl potassium xanthogenate in 50 ml. of alcohol at 0°–5° C. After 2 hours the precipitate is collected and dried to give 6 g. of ethyl 2-isobutyl-3-hydroxy-4-hydroxymethyl-5-pyridylmethylxanthate, m.p. 155°–156° C. (dec.).

Step C: Preparation of bis(2-isobutyl)-3-hydroxy-4-hydroxymethyl-5-pyridylmethyl)disulfide, dihydrochloride The xanthate product (6 gm.) from Step B in 50 ml. of concentrated ammonium hydroxide and 100 ml. of ethanol was stirred overnight at room temperature. The oily residue was extracted into 2 × 100 ml. of methylene chloride and dried over magnesium sulfate. The solution was filtered and treated with dry gaseous hydrogen chloride at 0° C. The precipitate was collected on a filter and dried to give bis(2-isobutyl-3-hydroxy-4- hydroxymethyl-5-pyridylmethyl)disulfide, dihydrochloride, m.p. 180°–182° C.

Employing substantially the same procedure as described in Example 4, but using 2-methyl-4,5-di(hydroxymethyl)pyridine hydrochloride as starting materials, there is produced in sequence:

Step A: 2-methyl-4,5-di(bromomethyl)pyridine hydrobromide;
Step B: ethyl 2-methyl-4-hydroxymethyl-5-pyridylmethylxanthate; and
Step C: bis[2-methyl-4-hydroxymethyl-5-pyridylmethyl]-disulfide, m.p. 185°–189° C.

EXAMPLE 5

2-Methyl-3-Hydroxy-4-Mercaptomethyl-5-Methoxymethylpyridine, hydrochloride

Step A: Preparation of 2-methyl-3,4α-di-O-isopropylidene-5-methoxymethylpyridine A solution of 2 equivalents of sodium methoxide in one liter of methanol is prepared. To this is added one equivalent of 3,4α-di-O-isopropylidene derivative of 2-methyl-3-hydroxy-4-hydroxymethyl-5-chloromethyl pyridine hydrochloride and the solution refluxed with stirring for 3 hours. The reaction is concentrated in vacuo and the residue partitioned between one liter of water and one liter of ether. After drying over magnesium sulfate evaporation of the ether in vacuo affords the desired product.

Step B: Preparation of 2-methyl-3-hydroxy-4-hydroxymethyl-5-methoxymethylpyridine The above product, one equivalent, is dissolved in one liter of 2.5 N hydrochloric acid and is heated at 50°–60° C. for one hour. The reaction mixture is then quenched on excess sodium bicarbonate and the resulting precipitate is isolated, washed with water and dried.

Step C: Preparation of 2-methyl-3-hydroxy-4-mercaptomethyl-5-methoxymethylpyridine, hydrochloride Prepared by the process of Example 1, to give 2-methyl-3-hydroxy-4-mercaptomethyl-5-methoxymethylpyridine, hydrochloride, m.p. 144°–146° C.

EXAMPLE 6

2-Methyl-3-Hydroxy-4-Hydroximinomethyl-5-Mercaptomethylpyridine

Step A: Preparation of 2-methyl-3-hydroxy-4-hydroximinomethyl-5-chloromethylpyridine hydrochloride A solution of 18.2 g. of 2-methyl-3-hydroxy-4-hydroximinomethyl-5-hydroxymethylpyridine and 11.9 g. of thionylchloride in 100 ml. of ether and 100 ml. of chloroform was refluxed 6 hours. The cooled mixture was filtered and the solids were washed with ether to give 21.0 g. of 2-methyl-3-hydroxy-4-hydroximinomethyl-5-chloromethylpyridine hydrochloride, m.p. 167°–171° C. (dec.).

Step B: Preparation of 2-methyl-3-hydroxy-4-hydroximino-5-isothioureido methylpyridine dihydrochloride A mixture of 21.0 g. of the chloromethyl compound from Step A, 6.74 g. of thiourea, and 200 ml. of ethanol was refluxed 3 hours. The cooled mixture was filtered and the solids were washed with ether to give 9.86 g. of 2-methyl-3-hydroxy-4-hydroximino-5-isothioureido methylpyridine dihydrochloride, m.p. 229°–230° C.

Step C: Preparation of 2-methyl-3-hydroxy-4-hydroximinomethyl-5-mercaptomethylpyridine hydrochloride A mixture of 9.0 g. of the isothioureido compound of Step B, and 60 ml. of 6.5% (w/v) potassium hydroxide was refluxed 4 hours. A black solid was filtered off, and the filtrate was acidified with acetic acid and evaporated to dryness. The residue was extracted with 40 ml. of water and 200 ml. of ether. The aqueous phase was separated, acidified with concentrated hydrochloric acid, basified with sodium bicarbonate solution and extracted with ethyl acetate. Evaporation to dryness gave 2-methyl-3-hydroxy-4-hydroximinomethyl-5-mercaptomethylpyridine, m.p. 255°–260° C. (dec.).

EXAMPLE 7

2,4-Dimethyl-3-Hydroxy-5-Mercaptomethylpyridine

Step A: Preparation of 2-methyl-3-acetoxy-4-hydroxymethyl-5-acetoxymethylpyridine One equivalent of 2-methyl-3-acetoxy-4-formyl-5-acetoxymethylpyridine in 1 liter of anhydrous diethyl ether is treated with 1.5 equivalents of sodium borohydride and aged 3 hours at room temperature. The reaction mixture is quenched on excess aqueous ammonium chloride solution and the ether layer is separated. After magnesium sulfate drying, concentation in vacuo gives the desired product.

Step B: Preparation of 2-methyl-3-acetoxy-4-p-toluenesulfonyloxymethyl-5-acetoxymethylpyridine One equivalent of the above product in one liter of pyridine is treated with one equivalent p-toluenesulfonyl chloride and the reaction mixture aged 6 hours at room temperature. The reaction mixture is concentrated in vacuo and the residue partitioned between 1 liter water and one liter chloroform. After separation, the chloroform layer is dried over magnesium sulfate and concentrated in vacuo to afford the desired tosylate.

Step C: Preparation of 2,4-dimethyl-3-hydroxy-5-hydroxymethylpyridine

One equivalent of the above product in one liter of ether is added to 4 equivalents lithium aluminum hydride in 2 liters ether. The reaction mixture is aged 3 hours at room temperature. Excess hydride is spent by the introduction of ethylacetate. The reaction mixture is quenched on 2 liters of water saturated with ammonium chloride. The layers are cut and the aqueous phase extracted with 500 ml. ethylacetate. The combined organic phases are dried over magnesium sulfate and concentrated in vacuo to afford the desired product.

Step D: Preparation of 2,4-dimethyl-3-hydroxy-5-chloromethylpyridine hydrochloride The above product, one equivalent, is dissolved in one liter of tetrahydrofuran and one equivalent thionyl chloride introduced. After 3 hours reflux, the reaction mixture is cooled and the desired product isolated by filtration.

Step E: Preparation of 2,4-dimethyl-3-hydroxy-5-(ethylxanthato)methylpyridine The above product, one equivalent, in one liter absolute ethanol is added dropwise to a solution of 3.5 equivalents potassium ethylxanthate in 2 liters of water at 0°–5° C., at such a rate that the temperature does not exceed 10° C. After addition, the reaction is aged one hour at 5°–10° C. and 4 hours at room temperature. The reaction mixture is quenched on 1.5 liters of ether and shaken well. After separation, the ether layer is dried over magnesium sulfate and evaporated in vacuo to afford the desired product.

Step F: Preparation of 2,4-dimethyl-3-hydroxy-5-mercaptomethylpyridine

The above product, one equivalent, is dissolved in one liter of 2.5 N sodium hydroxide solution and heated at 50°–60° C. for 3 hours. After cooling, the pH is adjusted to 6.0 and the resulting precipitate isolated, washed with water, and dried.

EXAMPLE 8

2,4-Dimercaptomethyl-3-Hydroxy-5-Hydroxymethylpyridine Hydrochloride

The 2,4,5-tri(hydroxymethyl)-3-hydroxypyridine hydrochloride (3.0 gm.) was dissolved in a stirred solution of sodium hydroxide (6.0 g.) in absolute ethanol (60 ml.) under nitrogen. After 1 hour the reaction was cooled to 20° C. and carbon disulfide was added (9 ml.) all at once. The reaction was stirred for 2 hours at room temperature and then for 5 hours at reflux. The reaction mixture was evaporated to ½ volume, cooled to 5° C., and acidified with concentrated hydrochloric acid. The mixture was evaporated to absolute dryness under high vacuum at <60° C.

The solid residue was extracted with stirred boiling isopropanol (2 × 300 ml.), filtered and evaporated to give an oil. The oil was stirred in evaporating boiling benzene and then evaporated to dryness. The oil was dissolved in tetrahydrofuran (100 ml.), stirred, and cooled in an ice-salt bath as gaseous hydrogen chloride was bubbled in. The precipitated 2,4-dimercaptomethyl-3-hydroxy-5-hydroxymethylpyridine hydrochloride (1.7 g.), m.p. 95°–97° was collected.

EXAMPLE 9

2-Methyl-3-Hydroxy-4-Mercaptomethylpyridine-5-Acetic Acid

Step A: Preparation of 3-O-4α-s-isopropylidene derivative of 2-methyl-3-hydroxy-4-mercaptomethyl-5-hydroxymethylpyridine Gaseous hydrogen chloride was bubbled through a solution of 20 g. of 4-mercaptopyridoxine hydrochloride suspended in 400 ml. of acetone between −5° C. and 0° C. When solution had occurred, the temperaure was permitted to rise spontaneously to 20° C. with continued introduction of hydrogen chloride. After 1 hour at 20°–25° C., the mixture was recooled to 0° C., saturated with hydrogen chloride, and held at 0° C. for 3 hours. The solution was diluted with 2 liters of ether. The resulting precipitate was collected, suspended in 300 ml. of ethanol, and adjusted to about pH 8 with methanolic sodium methoxide. The precipitated sodium chloride was removed by filtration and there was added to the filtrate, about 50 g. of chromatographic silica gel. The mixture was concentrated to dryness and the residue was chromatographed on silica gel by elution with acetone-ether (1v/2v). The proper fractions were combined and concentrated to dryness to give 3-O-4α-S-isopropylidene derivative of 2-methyl-3-hydroxy-4-mercaptomethyl-5-hydroxymethylpyridine, m.p. 184°–186° C.

Step B: Preparation of 3-O-4α-S-isopropylidene derivative of 2-methyl-3-hydroxy-4-mercaptomethyl-5-chloromethylpyridine hydrochloride The product from Step A(11.25 g.) was suspended in 400 ml. benzene and heated to 40°–50° C. Thionyl chloride (15 ml.) was added cautiously and the mixture was allowed to cool to room temperature. After 1 hour at room temperature, the mixture was cooled to 10° C. and precipitate was collected to give 13.2 g of 3-O-4α-S-isopropylidene derivative of 2-methyl-3-hydroxy-4-mercaptomethyl-5-chloromethylpyridine hydrochloride, m.p. 198°–201° dec.

Step C: Preparation of 3-O-4α-S-isopropylidene derivative of 2-methyl-3-hydroxy-4-mercaptomethyl-5-cyanomethylpyridine To a slurry of 13 g. of the chloromethyl compound from Step B in 300 ml. of acetone was added 25 g. of sodium cyanide in 60 ml. of water. The mixture was refluxed overnight, cooled and the acetone was removed by distillation. Water (200 ml.) was added and the mixture was extracted with methylene chloride. The extracts were dried and concentrated to dryness to yield 11 g. of crude 3-O-4α-S-isopropylidene derivative of 2-methyl-3-hydroxy-4-mercaptomethyl-5-cyanomethylpyridine as an oil which was used directly in the next step.

Step D: Preparation of 3-O-4α-S-isopropylidene derivative of 2-methyl-3-hydroxy-4-mercaptomethyl-5-carboxymethylpyridine The crude nitrile from Step C (11.0 g.) in a mixture of 15 g. of sodium hydroxide and 400 ml. of 70% ethanol was refluxed for 5 hours. The mixture was concentrated to dryness, and the residue was dissolved in a small volume of water, and carefully adjusted to pH 5–6 with hydrochloric acid. The resulting precipitate was collected on a filter, washed with cold water and dried, to give 7.5 g. of 3-O-4α-S-isopropylidene derivative of 2-methyl-3-hydroxy 4-mercaptomethyl-5-carboxymethylpyridine, m.p. 235°–236° dec.

Step E: Preparation of 2-methyl-3-hydroxy-4-mercaptomethylpyridine-3-acetic acid A mixture of 2.0 g. of the product from Step D in 50 ml. of 2.5 N hydrochloric acid was heated for 30 minutes on a steam bath. The cooled mixture was filtered, and the filtrate was concentrated to dryness, triturated with 7–8 ml. isopropanol, and the solids were collected and washed with isopropanol-ether and ether to give 2-methyl-3-hydroxy-4-mercaptomethylpyridine-3-acetic acid, m.p. 185°–187° C.

EXAMPLE 10

2-Methyl-3-Methoxy-4-Hydroxymethyl-5-Mercaptomethylpyridine

An excess of diazomethane in ether was added to 5-mercaptopyridoxine in isopropanol solution at room temperature. After standing overnight the mixture was washed with water, dried over magnesium sulfate and concentrated to dryness. The residue was triturated with ethylacetate and collected on a filter to give 2-methyl-3-methoxy-4-hydroxymethyl-5-mercaptomethylpyridine, m.p. 227°–230° C. (dec.).

EXAMPLE 11

2-Methyl-3-Hydroxy-4-Dimethylaminomethyl-5-Mercaptomethylpyridine

Step A: Preparation of 2-methyl-3-hydroxy-4-dimethylaminomethyl-5-hydroxymethylpyridine A mixture of 7.2 g. of pyridoxamine, 7.5 g. of formaldehyde (20 ml. of 37% solution) and ½ teaspoon of Raney nickel was hydrogenated at 40 p.s.i. and room temperature for 16 hours. The mixture was filtered, and the filtrate was evaporated to dryness to give 3.8 g. of 2-methyl-3-hydroxy-4-dimethylaminomethyl-5-hydroxymethylpyridine, m.p. 146°–151° C.

Step B: Preparation of 2-methyl-3-hydroxy-4-dimethylaminomethyl-5-bromomethylpyridine dihydrobromide The product from Step A (3.8 g.) was refluxed in concentrated hydrobromic acid (100 ml.) for 10 minutes and cooled in an ice-bath. The solution was evaporated to about 50 ml. and the resulting solid was collected on a filter and dried to give 2.4 g. of 2-methyl-3-hydroxy-4-dimethylaminomethyl-5-bromomethylpyridine dihydrobromide, which was used directly in the next step.

Step C: Preparation of ethyl 2-methyl-3-hydroxy-4-dimethylaminomethyl-5-pyridylmethylxanthate The bromomethyl compound (2.4 g.) from Step B in 200 ml. of water was added to a cooled solution of 15 g. of potassium ethyl xanthogenate in 60 ml. of water over 20 minutes with stirring while maintaining the temperature at 5°–10° C. After 2 days, the solution was extracted with ether. The ether extract was dried over magnesium sulfate and then molecular sieves overnight. Concentration to dryness gave ethyl 2-methyl-3-hydroxy-4-dimethylaminomethyl-5-pyridylmethylxanthate as an oil.

Step D: Preparation of 2-methyl-3-hydroxy-4-dimethylaminomethyl-5-mercaptomethylpyridine The xanthate (13.5 g.) from Step C in 200 ml. of tetrahydrofuran:ether (3:1 v/v) was added to lithium aluminum hydride under ether and nitrogen at 0° C. over 30 minutes. After stirring one hour at room temperature, it was poured into a mixture of tetrahydrofuran and saturated ammonium chloride solution. The water layer was separated and extracted with 2 × 400 ml. of tetrahydrofuran. The combined tetrahydrofuran solutions were dried and evaporated to an oil which on trituration with ethylacetate gave 6.0 g. of 2-methyl-3-hydroxy-4-dimethylaminomethyl-5-mercaptomethylpyridine, m.p. 92°–94° C. (dec.).

EXAMPLE 12

Bis(2-Methyl-3-Hydroxy-4-Dimethylaminomethyl-5-Pyridylmethyl) Disulfide

Ethyl-2-methyl-3-hydroxy-4-dimethylaminomethyl-5-pyridylmethylxanthate (see Example 11, Step C) (41 g.) was stirred in 300 ml. of a 1:1 (v/v) mixture of ethanol and concentrated ammonium hydroxide for 3 days at room temperature. The resulting gummy solid was extracted with 3 × 300 ml. of ethyl acetate. The extract was dried over magnesium sulfate, and evaporated to dryness. The residue slowly crystallized to give 3 g. of bis(2-methyl-3-hydroxy-4-dimethylaminomethyl-5-pyridylmethyl)disulfide, m.p. 195°–201° C.

EXAMPLE 13

2-Methyl-3-Hydroxy-4-Mercaptomethyl-5-(1-Hydroxyethyl) Pyridine Hydrochloride

Step A: Preparation of 3,4α-di-O-isopropylidene derivative of 2-methyl-3-hydroxy-4-hydroxymethyl-5-(1-hydroxyethyl)pyridine A solution of 14.8 g. of 3,4α-di-O-isopropylidene derivative of 2-methyl-3-hydroxy-4-hydroxymethyl-5-formyl pyridine in 100 ml. of ether was treated at 15° C. with 22.3 ml. of 3 N methyl magnesium chloride in tetrahydrofuran dropwise with stirring. The reaction mixture was aged at ambient temperature overnight, then quenched in 300 ml. of ice water containing 10 g. of ammonium chloride. The aqueous layer was separated and extracted with ether. The combined ether layers were dried over magnesium sulfate and concentrated to dryness to give 10 g. of the 3,4α-di-O-isopropylidene derivative of 2-methyl-3-hydroxy-4-hydroxymethyl-5-(1-hydroxyethyl) pyridine, m.p. 105°–112° C.

Step B: Preparation of 2-methyl-3-hydroxy-4-hydroxymethyl-5-(1-hydroxyethyl)pyridine hydrochloride The oil from Step A above was dissolved in 1 N hydrochloric acid (300 m.) and the mixture was heated for 1 hour. The aqueous solution was cooled and extracted with ether (2 × 300 ml.). The aqueous layer was evaporated to dryness at 40° under high vacuum. The oily product was dissolved in ether (100 ml.) and dry hydrogen chloride gas was bubbled through it. The 2-methyl-3-hydroxy-4-hydroxymethyl-5-(1-hydroxyethyl)pyridine hydrochloride crystallized out, and was collected and dried, m.p. 160°–164° (dec.).

Step C: Preparation of 2-methyl-3-hydroxy-4-mercaptomethyl-5-(1-hydroxyethyl) pyridine hydrochloride Prepared by the process described in Example 1, the product being recrystallized from isopropanol to give 2-methyl-3-hydroxy-4-mercaptomethyl-5-(1-hydroxyethyl) pyridine hydrochloride, m.p. 174°–175° C.

Example 14

2-Methyl-3-Hydroxy-4-Hydroxymethyl-5-(1-Mercaptoethyl) Pyridine Hydrochloride

Step A: Preparation of 3,4α-di-O-isopropylidene derivative of 2-methyl-3-hydroxy-4-hydroxymethyl-5-(1-chloroethyl)pyridine A mixture of 14 g. of 3,4α-di-O-isopropylidene derivative of 2-methyl-3-hydroxy-4-hydroxymethyl-5-(1-hydroxyethyl)pyridine in 140 ml. of benzene and 5 ml. of thionyl chloride was refluxed for 2 hours. Concentration to dryness gave 16.46 g. of 3,4α-di-O-isopropylidene derivative of 2-methyl-3-hydroxy-4-hydroxymethyl-5-(1-chloroethyl)pyridine, m.p. 183°–186° C. (dec.).

Step B: Preparation of 3,4α-di-O-isopropylidene derivative of 2-methyl-3-hydroxy-4-hydroxymethyl-5-(1-mercaptoethyl)pyridine hydrochloride A solution of 20.36 g. of potassium ethylxanthogenate in 150 ml. of water was cooled to 0° C., and there was added to it dropwise with stirring 8.23 g. of chloromethyl compound from Step A in 200 ml. of ethanol while maintaining the temperature at 0°–5° C. After standing overnight at room temperature under an argon atmosphere, the mixture was diluted with 500 ml. water and extracted with 3 × 50 ml. of ether. The combined extracts were dried over magnesium sulfate and concentrated to a volume of 100 ml. The resulting solution was added dropwise under argon to a suspension of 15. g. of lithium aluminum hydride in 100 ml. of absolute ether. After one hour at room temperature, excess reagent was decomposed by dropwise addition of 20 ml. of water in 40 ml. of tetrahydrofuran, followed by 100 ml. of ice-water plus 15 g. of ammonium chloride. After one hour, the aqueous phase was separated, and extracted with 2 × 75 ml. ether. The combined original ether layer and the extracts were dried over magnesium sulfate and evaporated to an oily residue. The residue was dissolved in 50 ml. of tetrahydrofuran, cooled to 5° C., and saturated with dry hydrogen chloride, and made cloudy with ether. The resulting crystalline product (3.4 g.) was recrystallized from isopropanol-ether to give 3,4α-di-O-isopropylidene derivative of 2-methyl-3-hydroxy-4-hydroxymethyl-5-(1-mercaptoethyl)pyridine hydrochloride, m.p. >200° C. (dec.).

Step C: Preparation of 2-methyl-3-hydroxy-4-hydroxymethyl-5-(1-mercaptoethyl)pyridine hydrochloride A mixture of 2.0 g. of the mercaptoethyl compound from Step B, 6.0 ml. of 2.5 N hydrochloric acid and 10 ml. of water and heated at 50° C. for 45 minutes. The mixture was made alkaline with solid sodium bicarbonate and concentrated to dryness. The residue was extracted with 50 ml. of hot isopropanol. The extract was cooled to 0° C., saturated with dry hydrogen chloride and concentrated to dryness. The solid residue was isolated by trituration with ether and filtration and dried to give 1.26 g. of 2-methyl-3-hydroxy-4-hydroxymethyl-3-(1-mercaptoethyl)pyridine hydrochloride. After recrystallization from isopropanol-ether, it had m.p. >200° C. (dec.).

EXAMPLE 15

3,4α-Di-O-Isopropylidene Derivative of (−)-2-Methyl-3-Hydroxy-4-Hydroxymethyl-5-(1-Mercaptoethyl)Pyridine A solution of 7.75 g. of (+)-α-phenethylisocyanate in 50 ml. ether was added to 11.95 g. of the 3,4α-di-O-isopropylidene derivative of 2-methyl-3-hydroxy-4-hydroxymethyl-5-(1-mercaptoethyl)pyridine in 100 ml. ether and aged 2 hours at room temperature. The mixture was concentrated to dryness and the residue was dissolved in 100 ml. of tetrahydrofuran. This solution was saturated with hydrogen chloride at 0° C., then evaporated to dryness. The residue was triturated with acetone and the solid was collected (3.93 g., m.p. 233°–235° C.). Two recrystallizations from ethanol gave 2.5 g. of the S-(phenethylcarbomoyl) derivative, $[\alpha]_D$ −108.9°.

A sample of the derivative (1.5 g.) in 100 ml. of methanol was treated with excess triethylamine and the mixture was concentrated in vacuo. The residue was treated with 50 ml. of water and 50 ml. of ethyl acetate. The ethyl acetate layer was separated, dried over magnesium sulfate and concentrated to dryness. The residue was dissolved in 50 ml. of tetrahydrofuran and added dropwise with stirring to 1.0 g. of lithium aluminum hydride in 50 ml. of ether. After 1 hour at room temperature it was cooled to −5° C. and there was added dropwise under nitrogen a mixture of 20 ml. of water and 20 ml. of tetrahydrofuran. The mixture was then quenched in 100 ml. of water and extracted with 3 × 100 ml. of ethyl acetate. The extract was dried over magnesium sulfate, and concentrated to 0.70 gm. of oily 3,4α-di-O-isopropylidene derivative of (−)-2-methyl-3-hydroxy-4-hydroxymethyl-5-(1-mercaptoethyl)-pyridine, $[\alpha]_D$ −33.1° ± 0.5.

EXAMPLE 16

3,4α-Di-O-Isopropylidene Derivative of 2-Methyl-3-Hydroxy-4-Hydroxymethyl-5-(2-Mercaptoprop-2-yl)Pyridine

Step A: Preparation of 3,4α-di-O-isopropylidene derivative of 2-methyl-3-hydroxy-4-hydroxymethyl-5-acetyl pyridine To 750 ml. of dry methylene chloride containing 47.5 ml. of dry pyridine was added with stirring and cooling 29.6 g. of chromium trioxide. The mixture was aged 20 minutes at room temperature and then treated with a solution of 10.96 g. of the product from Example 13, Step A, in 250 ml. of dry methylene chloride over 15 minutes. After one hour at room temperature, the reaction mixture was filtered and the residue was washed with 2 × 100 ml. of methylene chloride. The methylene chloride filtrates were extracted with 3 × 500 ml. of 5% (w/w) aqueous sodium hydroxide solution, dried over magnesium sulfate and evaporated to dryness. The residue was crystallized from hexane to give 5.5 g. of 2-methyl-3-hydroxy-4-hydroxymethyl-5-acetyl-3,4α-di-O-isopropylidene pyridine.

Step C: Preparation of the 3,4α-di-O-isopropylidene derivative of 2-methyl-3-hydroxy-4-hydroxymethyl-5-(2-hydroxy-2-propyl)pyridine A solution of 3.93 g. of the product from Step B in 200 ml. of tetrahydrofuran was treated dropwise with 10% excess of methyl magnesium bromide in tetrahydrofuran. After aging 2 days at ambient temperature the reaction was quenched on ice-water (100 ml.) containing 10 g. of ammonium chloride. The aqueous layer was separated and extracted with ether. The combined organic layers were dried over magnesium sulfate and evaporated to dryness to give 4.14 g. of the 3,4α-di-O-isopropylidene derivative of 2-methyl-3-hydroxy-4-hydroxymethyl-5-(2-hydroxy-2-propyl)pyridine, which was used directly in the next step.

Step D: Preparation of 3,4α-di-O-isopropylidene derivative of 2-methyl-3-hydroxy-4-hydroxymethyl-5-(2-chloro-2-propyl)pyridine A solution of 4.14 g. of the product from Step C in 50 ml. of chloroform and 50 ml. of ether was treated with 1.57 ml. of thionyl chloride. The mixture was refluxed overnight and then concentrated to an oil. The residue was crystallized by dissolving it in 50 ml. of tetrahydrofuran and adding 25 ml. of ether, giving 1.81 g. of 3,4α-di-O-isopropylidene derivative of 2-methyl-3-hydroxy-4-hydroxymethyl-5-(2-chloro-2-propyl)pyridine.

Step E: Preparation of 3,4α-di-O-isopropylidene derivative of 2-methyl-3-hydroxy-4-hydroxymethyl-5-(2-mercaptoprop-2-yl)pyridine Prepared from the product of Step D above by the procedure of Example 14, Step B, to give the 3,4α-di-O-isopropylidene derivative of 2-methyl-3-hydroxy-4-hydroxymethyl-5-(2-mercaptoprop-2-yl)pyridine, m.p. 80.5°–82° C.

EXAMPLE 17

2-6-Di(Mercaptomethyl)pyridine

Step A: Preparation of 2,6-di(chloromethyl)pyridine hydrochloride

A mixture of 25 g. of 2,6-di(hydroxymethyl)pyridine, 29 ml. of thionyl chloride, and 200 ml. of tetrahydrofuran was refluxed with stirring for 4 hours. After cooling the precipitate was collected on a filter, washed with ether and dried to give 19.4 g. of 2,6-di(chloromethyl)pyridine hydrochloride, m.p. 143°–145° C.

Step B: Preparation of 2,6-di(mercaptomethyl)pyridine

A solution of 15 g. of 2,6-di(chloromethyl)pyridine in 500 ml. of ethanol was added dropwise with stirring under argon to 67 g. of potassium ethyl xanthogenate in 150 ml. water at 0°–5° C. After 2 days at room temperature mixture was diluted with 700 ml. water and extracted with ether. The combined extracts were dried over magnesium sulfate and concentrated to dryness.

The residue was refluxed with 100 ml. of 2.5 N sodium hydroxide solution for 3 hours under argon. After cooling the mixture was acidified with hydrochloric acid and concentrated to dryness and the residue was extracted with hot ethanol and salts were removed by filtration. After concentration to dryness, the residue was taken up in water, basified with sodium bicarbonate and extracted with ethyl acetate. The ethyl acetate extract was dried over magnesium sulfate and concentrated to an oil which was chromatographed on silica gel by elution with chloroform to give oily 2,6-di(mercaptomethyl)pyridine.

EXAMPLE 18

3,4α-Di-O-Isopropylidene Derivative of 2-Methyl-3-Hydroxy-4-Hydroxymethyl-5-(α-mercaptobenzyl)Pyridine Employing the procedure of Example 13, Step A, but substituting for the methyl magnesium chloride was used therein an equivalent amount of phenyl magnesium chloride, there is produced the 3,4α-di-O-isopropylidene derivative of 2-methyl-3-hydroxy-4-hydroxymethyl-5-(α-hydroxybenzyl)pyridine, m.p. 146°–150° C.

Employing this material in the procedures of Example 14, Steps A and B, there are produced respectively: 3,4α-di-O-isopropylidene derivative of 2-methyl-3-hydroxy-4-hydroxymethyl-5-(α-chlorobenzyl)-pyridine; and 3,4α-di-O-isopropylidene derivative of 2-methyl-3-hydroxy-4-hydroxymethyl-5-(α-mercaptobenzyl)pyridine, (an oil).

EXAMPLE 19

3,4α-Di-O-Isopropylidene Derivative of 2-Methyl-3-Hydroxy-4-Hydroxymethyl-5-Mercaptomethylpyridine-N-Oxide Step A: Preparation of 3,4α-di-O-isopropylidene derivative of 2-methyl-3-hydroxy-4-hydroxymethyl-5-chloromethylpyridine-N-oxide A sample of the 3,4α-di-O-isopropylidene derivative of 2-methyl-3-hydroxy-4-hydroxymethyl-5-chloromethylpyridine hydrochloride (132 g.) was added to excess aqueous sodium bicarbonate solution, and extracted into 2 × 70 ml. of chloroform. The extract was dried over magnesium sulfate and treated with 10.1 g. of m-chloroperbenzoic acid and aged over the weekend at room temperature. The mixture was extracted with 3 × 200 ml. of 5% sodium bicarbonate solution, dried over magnesium sulfate, and evaporated to dryness to give 9.6 g. of 3,4α-di-O-isopropylidene derivative of 2-methyl-3-hydroxy-4-hydroxymethyl-5-chloromethylpyridine-N-oxide, which was used directly in the next step.

Step B: Preparation of 3,4α-di-O-isopropylidene derivative of 2-methyl-3-hydroxy-4-hydroxymethyl-5-mercaptomethylpyridine-N-oxide A solution of 24.3 g. of the chloromethyl compound from Step A in 500 ml. of ethanol was added dropwise with stirring to a solution of 64 g. of potassium ethyl xanthogenate in 300 ml. of water at −5° C. to 0° C. under argon. After 1 hour at −5° C. to 0° C. and overnight at room temperature, it was quenched on 1 liter of ice-water. The mixture was extracted with 2 × 150 ml. ether. The extract was dried over magnesium sulfate and concentrated to dryness to give 31.2 g. of oil.

The oil was dissolved in 150 ml. of tetrahydrofuran and added dropwise with stirring under argon to a solution of 3.0 g. of lithium borohydride in 300 ml. ether. After 1½ hours at room temperature it was quenched with 300 ml. ice-water and 30 g. of ammonium chloride. The aqueous mixture was extracted with 3 × 150 ml. ethyl acetate which were dried over magnesium sulfate and evaporated to dryness to give 7.71 g. of 3,4α-di-O- isopropylidene derivative of 2-methyl-3-hydroxy-4-hydroxymethyl-5-mercaptomethylpyridine-N-oxide, m.p. 134°-135.5° C.

EXAMPLE 20

2-Mercaptomethyl-8-Methyl-2-Phenyl-4H-Dioxino[4,5-c]Pyridine

Step A: Preparation of 5,5'-(dithiodimethylene)bis[8-methyl-2-phenyl-4H-m-dioxino[4,5-c]pyridine]

A mixture of 0.01 moles of 5,5'-(dithiodimethylene)-bis[3-hydroxy-4-hydroxymethyl-2-methylpyridine] and 100 ml. of benzaldehyde was saturated with hydrogen chloride gas at 0°-5° and then stirred at this temperature for 4 hours. At this time 800 ml. of ether were added and the resulting precipitate was separated by filtration. This solid was then added to a well stirred mixture of 200 ml. chloroform and 200 ml. of water containing 20 gm. of sodium carbonate. After 15 minutes the chloroform layer was removed, dried, and concentrated to give an oil which gradually solidified. This solid was filtered with the aid of a small amount of ether to give 5,5'-(dithiodimethylene)bis[8-methyl-2-phenyl-4H-m-dioxino[4,5-c]pyridine].

Step B: Preparation of 5-mercaptomethyl-8-methyl-2-phenyl-4H-m-dioxino[4,5-c]pyridine To a suspension of 0.2 gm. of lithium aluminum hydride in 100 ml. of dry tetrahydrofuran was added 0.004 mole of 5,5'-(dithiodimethylene)bis[8-methyl-2-phenyl-4H-m-dioxino[4,5-c]pyridine]. The reaction mixture was stirred for 3 hours at 0°-5°. At this time there was added to the reaction mixture 100 ml. of benzene, 50 ml. of water, and 20 gm. ammonium chloride. The organic layer was separated and the aqueous extracted 2 times with 50 ml. of benzene. The combined benzene extracts were washed well with water, dried over sodium sulfate, and concentrated in vacuo. Chromatography on silica gel (250 gm.) and elution with ether gave 5-mercaptomethyl-8-methyl-2-phenyl-4H-m-dioxino[4,5-c]pyridine, m.p. 110°-112° C.

EXAMPLE 21

5-Mercaptopyridoxine Bunte Salt

A solution of 24.82 g. of sodium thiosulfate in 20 ml. of water was added to a solution of 26.4 g. of 3,4α-di-O-isopropylidene derivative of 2-methyl-3-hydroxy-4-hydroxymethyl-5-chloromethylpyridine hydrochloride in 200 ml. of 50% ethanol. The mixture was heated 1 hour at 75° C., cooled and evaporated to dryness. The residue on trituration with ethyl acetate gave 4.42 g. of 5-mercaptopyridoxine Bunte salt, m.p. 187°-190° C.

By the same procedure, there was prepared the Bunte salt of 2-methyl-3-hydroxy-4-aminomethyl-5-mercaptomethylpyridine, m.p. 270° C.

EXAMPLE 22

5-Mercaptopyridoxine Mixed Disulfide with Penicillamine, Dihydrochloride

The Bunte salt (0.01 mole) from Example 21, 0.01 mole of penicillamine and 3 molecular equivalents of sodium hydroxide (2.5 N aqueous solution) were warmed together on a steam bath for 2 hours. After cooling the mixture was extracted with 2 × 50 ml. of ethyl acetate. The extract was dried over magnesium sulfate and concentrated to dryness. The residue was taken up in tetrahydrofuran and treated with hydrogen chloride which caused precipitation of 5-mercaptopyridoxine mixed disulfide with penicillamine, dihydrochloride, m.p. 171°-175° C. (dec.).

EXAMPLE 23

Bis[2-Methyl-3-Hydroxy-4-Hydroxymethyl-5-Pyridyl(1-ethyl)] Disulfide Dihydrochloride Following the procedure of Example 21, the Bunte salt of the 3,4α-isopropylidene derivative of 2-methyl-3-hydroxy-4-hydroxymethyl-5-(1-mercaptoethyl)pyridine was prepared from the corresponding 5-(1-chloroethyl) analog. After concentrating the reaction mixture to dryness, the product was extracted into isopropanol which was concentrated to an oil. The oil was refluxed 18 hours with 1 N sulfuric acid. This was concentrated to dryness, the residue was taken up in isopropanol, filtered, and again evaporated to an oil. The oil was treated with aqueous sodium bicarbonate solution. The resulting solid was collected, dissolved in isopropanol and treated with gaseous hydrogen chloride. Addition of ether caused crystallization of bis[2-methyl-3-hydroxy-4-hydroxymetyl-5-pyridyl(1-ether)]disulfide dihydrochloride, m.p. 143°-144° C.

EXAMPLE 24

Bis[2-Methyl-3-Benzoyloxy-4-Benzoyloxymethyl-5-Pyridylmethyl]Disulfide Dihydrochloride A solution of 3.68 g. of pyrithioxine and 6.33 g. of benzoyl chloride in 40 ml. of pyridine was refluxed 2 hours. After evaporating to dryness the residual oil was dissolved in chloroform, washed with water and dried over magnesium sulfate. The filtered chloroform solution was treated with gaseous hydrochloric acid and evaporated to near dryness. Trituration with acetonitrile gave a solid which was recrystallized from acetonitrile to give bis[2-methyl-3-benzoyloxy-4-benzoyloxymethyl-5-pyridylmethyl]disulfide dihydrochloride, m.p. 185°-189° C.

Employing substantially the same procedure as in Example 24 but substituting for the benzoyl chloride used therein, equivalent amounts of acetyl chloride and cyclopropanecarbonyl chloride, there are produced respectively:

Bis[2-methyl-3-acetoxy-4-acetoxymethyl-5-pyridylmethyl] disulfide dihydrochloride, and
Bis[2-methyl-3-cyclopropanecarbonyloxy-4-cyclopropanecarbonyloxymethyl-5-pyridylmethyl]disulfide dihydrochloride, m.p. 168°-170° C.

EXAMPLE 25

2-Methyl-3-Benzoyloxy-4-Benzoyloxymethyl-5-Mercaptomethylpyridine

A mixture of 1 g. of bis[2-methyl-3-benzoyloxy4-benzoyloxymethyl-5-pyridylmethyl]disulfide dihydrochloride, 2 g. of zinc dust and 20 m. acetic acid was stirred at room temperature overnight under nitrogen. The mixture was filtered and extracted well with chloroform. The chloroform was washed with water, aqueous sodium bicarbonate, water dried over magnesium sulfate, and evaporated to dryness. The residue was recrystallized from chloroform to give 2-methyl-3-benzoyloxy-4-benzoyloxymethyl-5-mercaptomethylpyridine, m.p. 185°-189° C.

Employing the procedure of Example 25 but substituting for the benzoate ester disulfide used therein equivalent amounts of the corresponding acetate and cyclopropylcarbonyl ester there are produced respectively:

2-methyl-3-acetoxy-4-acetoxymethyl-5-mercaptomethylpyridine, m.p. 139°–141° C., and
2-methyl-3-cyclopropylcarbonyloxy-4-cyclopropylcarbonyloxymethyl-5-mercaptomethylpyridine, m.p. 168°–170° C.

EXAMPLE 26

Carbonate Esters of 5-Mercaptopyridoxine

To a mixture of 0.1 moles of 2-methyl-3-hydroxy-4-hydroxymethyl-5-mercaptomethylpyridine in 300 ml. of pyridine and 300 ml. of chloroform which was stirred under nitrogen at 0° was added a solution of 0.15 moles of ethylchloroformate in 100 ml. of chloroform. The reaction mixture was stirred at room temperature for 5 hours, concentrated in vacuo and the residue taken up between benzene-water (1:1) and made alkaline with solid sodium bicarbonate. The benzene layer was removed and the aqueous layer was extracted with 2 × 100 ml. benzene. The combined benzene extracts were dried and concentrated in vacuo. Chromatography of the residue on 2000 gm. of silica gel and elution with ether-petroleum ether (50–100%) gave the following carbonates of 2-methyl-3-hydroxy-4-hydroxymethyl-5-mercaptomethylpyridine as oils:

2-methyl-3-ethoxycarbonyloxy-4-ethoxycarbonyloxymethyl-5-ethoxycarbonylthiomethylpyridine,
2-methyl-3-ethoxycarbonyloxy-4-ethoxycarbonyloxymethyl-5-mercaptomethylpyridine,
2-methyl-3-hydroxy-4-ethoxycarbonyloxymethyl-5-ethoxycarbonylthiomethylpyridine, and
2-methyl-3-hydroxy-4-ethoxycarbonyloxymethyl-5-mercaptomethylpyridine.

Following the procedure of Example 26 but substituting for the ethylchloroformate used therein, equivalent amounts of adamantanoyl chloride, cyclopropylcarbonyl chloride, 2-acetoxysalicyloyl chloride, benzoyl chloride, 2-hydroxy-4-(2,3-difluorophenyl)benzoyl chloride, 3-chloro-4-allyloxyphenylacetyl chloride, α-methyl-4-isobutylphenylacetyl chloridie, α-methyl-3-phenoxyphenylacetyl chloride, α-methyl-3-benzoylphenylacetyl chloride, α-methyl-6-methoxynaphth-2-ylacetyl chloride, α-methyl-3-fluoro-4-phenylphenylacetyl chloride, 4-(3-chloro-4-cyclohexylphenyl)-4-ketobutyryl chloride, 2-(3-trifluoromethylanilino)benzoyl chloride, 2-(2,3-dimethylanilino)benzoyl chloride, 2-(2,6-dichloro-3-methylanilino)benzoyl chloride, 2-(3-trifluoromethylanilino)nicotinoyl chloride, 2-(2-methyl-3-chloroaninicotinoyl chloride, there are produced respectively the S-mono-, di-O-, 4-O-S-di- and tri adamantanoyl, cyclopropanoyl, 2-acetoxybenzoyl, benzoyl, 2-hydroxy-4-(2,4-difluorophenyl)benzoyl, 3-chloro-4-allyloxyphenylacetyl, α-methyl-4-isobutylphenylacetyl, α-methyl-3-phenoxyphenylacetyl, α-methyl-3-benzoylphenylacetyl, α-methyl-6-methoxynaphth-2-ylacetyl, α-methyl-3-fluoro-4-phenylphenylacetyl, 4-(3-chloro-4-cyclohexylphenyl)-4-ketobutyryl, 2-(3-trifluoromethylanilino)benzoyl, 2-(2,3-dimethylanilino)benzoyl, 2-(2,6-dichloro-3-methylanilino)benzoyl, 2-(3-trifluoromethylanilino)-nicotinoyl, 2-(2-methyl-3-chloroanilino)nicotinoyl derivatives of 2-methyl-3-hydroxy-4-hydroxymethyl-5-mercaptomethylpyridine.

Similarly, using allylchloroformate or other $C_{2-5}$ alkenylchloroformates in the above reaction produces the S-mono-, di-O-, 4-O,S-di and tri- alkenyloxycarbonyl derivatives of 5-mercaptopyridoxine.

EXAMPLE 27

Bis[2-Methyl-3-Hydroxy-4-Hydroxymethyl-6-Ethoxy-5-Pyridylmethyl]Disulfide

A mixture of 10 g. of pyrithioxine and 80 ml. of trifluoroacetic acid, was cooled to 0° C. and irradiated with U.V. light. Over 2.5 hours, 3.1 ml. of fluoroxytrifluoromethane was added. Irradiation was continued for 1.5 hours more. The solvent was evaporated and the residue was dissolved in 50 ml. of water and added to excess sodium bicarbonate solution. An insoluble gum was separated, dissolved in methanol, dried over magnesium sulfate. Silica gel was added and the suspension was evaporated to dryness. Attempts to chromatograph this on a silica gel column by elution with ethanol failed. Elution with chloroform-methanol (1:1 v/v) was successful. The later fractions yieldisng 4.7 g. of bis[2-methyl-3-hydroxy-4-hydroxymethyl-6-ethoxy-5-pyridylmethyl]disulfide. The procedure was designed to provide the 6-fluoro analog, but the product actually isolated was 6-ethoxy.

EXAMPLE 28

Pyridoxine-5-Thiophosphonic Acid

Step A: Preparation of 3,4α-di-O-isopropylidene derivative of sodium pyridoxine-5-phosphorothioate

Trisodium phosphorothioate (1.8 g., 0.01 mole) in water (5 ml.) is run into a solution of 3,4-di-O-isopropylidene derivative of 5-chloropyridoxine hydrochloride (2.07 g., 0.01 mole) in water (15 ml.) at 0°. The solution is stirred overnight at 10°. The solution is diluted with methanol and the solid 3,4α-di-O-isopropylidene derivative of pyridoxine-5-phosphorothioate filtered off.

Step B: Preparation of Pyridoxine-5-thiophosphonic acid

The above compound (3.26 g., 0.01 mole) in water (40 ml.) is acidified to pH 1 with dilute hydrochloric acid, and kept there for 20 minutes. Methanol is added to precipitate the subject compound as an internal salt.

Example 29

2-Methyl-3-Adamantanoyloxy-4-Adamantanoyloxymethyl-5-Mercaptomethylpyridine and

2-Methyl-3-Hydroxy-4-Adamantanoyloxymethyl-5-Mercaptomethylpyridine

To a mixture of 0.05 mole of 3-hydroxy-4-hydroxymethyl-5-mercaptomethyl-2-methylpyridine in 200 ml. of pyridine and 200 ml. of chloroform which is stirred under nitrogen at 0° to 5° is added a solution of 0.1 moles of 1-adamantane carbonyl chloride in 100 ml. of chloroform. The reaction mixture is stirred at room temperature for 3 hours and then concentrated in vacuo. The residue is taken up in a 1:1 mixture of benzene-water (600 ml.) and made alkaline with solid sodium bicarbonate. The benzene layer is removed and the aqueous layer extracted 2 times with 100 ml. of benzene. The combined benzene extracts are dried over sodium sulfate and concentrated in vacuo. Chromatography of the residue on 1000 gm. of silica gel and elution with ether-petroleum ether (25–100%) gives 2-methyl-3-adamantanoyloxy-4-adamantanoyloxymethyl-5-mercaptomethylpyridine, m.p. 129°–131° C., and 2-methyl-3-hydroxy-4-adamantanoyloxymethyl-5-mercaptomethylpyridine, m.p. 170°–172° C.

EXAMPLE 30

Di(3,4α-di-O-isopropylidene) Derivative of Bis[2-methyl-3-hydroxy-4-hydroxymethyl-5-pyridylmethyl]disulfide-di-N-Oxide A solution of one part of the 3,4α-di-O-isopropylidene derivative of 2-methyl-3-hydroxy-4-hydroxymethyl-5-mercaptomethylpyridine-N-oxide in 15 parts tetrahydrofuran was prepared. Through this solution air was bubbled for 3 days. The resulting precipitate was isolated and air dried. The desired disulfide had a melting point of 217°–219° C. (dec.).

EXAMPLE 31

S,S'-bis(3-hydroxy-4-hydroxymethyl-2-methyl-5-pyridylmethyl)carbonodithioate Dihydrochloride Monohydrate Step A: Preparation of S,S'-bis(2,2,8-trimethyl-4H-1,3-dioxino[4,5-c]pyridin-5-yl methyl carbonodithioate To an ice cooled solution of 4.5 gm. of 5-mercaptomethyl-2,2,8-trimethyl-4H-1,3-dioxino[4,5-c]pyridine in 50 ml. of dry pyridine was added dropwise 10 ml. of a 12.5% solution of phosgene in benzene. The reaction mixture was allowed to come to room temperature and stirred for three hours after which time it was concentrated in vacuo. The residue was extracted between benzene and saturated sodium bicarbonate solution. The benzene layer was separated, washed with water, dried over sodium sulfate and concentrated in vacuo. The residue was chromatographed on 250 gm. of silica gel. Elution with ether gave 3.59 gm. of S,S'-bis(2,2,8-trimethyl-4H-1,3-dioxino-[4,5-c]pyridin-5-yl methyl carbonodithioate, m.p. 88°–90°.

Step B: Preparation of S,S'-bis(3-hydroxy-4-hydroxymethyl-2-methyl-5-pyridyl methyl)carbonodithioate dihydrochloride monohydrate A solution of 0.2 gm. of S,S'-bis(2,2,8-trimethyl-4H-1,3-dioxino[4,5-c]pyridin-5-yl methyl carbonodithioate in 0.9 ml. of ice cold concentrated hydrochloric acid was stirred cold for 5 minutes after which time it was diluted to 2.5 ml. with methanol. Cooling in ice-acetone yielded a crystalline precipitate which was filtered to give 0.120 gm. of S,S'-bis(3-hydroxy-4-hydroxymethyl-2-methyl-5-pyridyl methyl)carbonodithioate dihydrochloride monohydrate, m.p. 125°130°.

EXAMPLE 32

S-(3-hydroxy-4-hydroxymethyl-2-methyl-5-pyridylmethyl) Phosphorothionate

To a solution of 0.95 gm. of 5-bromomethyl-3-hydroxy-4-hydroxymethyl-2-methylpyridine hydrobromide in 25 ml. of methanol stirred at room temperature was added 0.54 gm. of sodium thiophosphate and 1 ml. of water. The mixture was stirred for 1 hour during which time a precipitate formed. The reaction mixture was concentrated in vacuo to a solid which was collected by filtration with the aid of about 10 ml. of ice water and air dried to give 0.23 gm. of the sodium salt of the product. A mixture of 0.1 gm. of the above sodium salt in 1.5 ml. of glacial acetic acid was stirred at room temperature for 45 minutes. The precipitate was collected by filtration and washed with ether to give 0.06 gm. of S-(3-hydroxy-4-hydroxymethyl-2-methyl-5-pyridylmethyl)phosphorothionate, m.p. 177°–178°.

EXAMPLE 33

S,S'-bis(3-hydroxy-4-hydroxymethyl-2-methyl-5-pyridylmethyl)1,3-benzenedicarbothioate Step A: Preparation of S,S'-bis(2,2,8-trimethyl-4H-1,3-dioxino[4,5-c]pyridine-5-yl methyl) 1,3-benzenedicarbothioate To a solution of 4.5 gm. (0.02 mole) of 5-mercaptomethyl-2,2,8-trimethyl-4H-1,3-dioxino[4,5-c]pyridine in 50 ml. of pyridine and 50 ml. of chloroform was added dropwise with stirring a solution of 2.0 gm. (0.01 mole) of isophthaloyl dichloride in 50 ml. of chloroform. The reaction mixture was stirred overnight at room temperature and then concentrated in vacuo. The residue was extracted between benzene and saturated sodium bicarbonate solution. The benzene layer was separated, washed with water, dried over sodium sulfate and concentrated in vacuo to give 6.5 gm. of oil. Chromatography on 1,000 gm. of silica gel and elution with ether afforded 3.10 gm. of S,S'-bis(2,2,8-trimethyl-4H-1,3-dioxino[4,5-c]pyridin-5-yl methyl) 1,3-benzenedicarbothioate, m.p. 125°–127°, (soft. 120°).

Step B: Preparation of S,S'-bis(3-hydroxy-4-hydroxymethyl-2-methyl-5-pyridylmethyl) 1,3-benzenedicarbothioate A mixture of 0.100 gm. of S,S'-bis(2,2,8-trimethyl-4H-1,3-dioxino[4,5-cl]pyridin-5-yl methyl 1,3-benzene dicarbothioate and 0.5 ml. of concentrated hydrochloric acid was stirred for 5 minutes. The above solution was then neutralized by the addition of saturated sodium bicarbonate solution. The solid which separated was collected by filtration and air dried. Recrystallization from dimethylformamide and water gave 0.04 gm. of S,S'-bis(3-hydroxy-4-hydroxymethyl-2-methyl-5-pyridylmethyl) 1,3-benzenedithiocarbothioate, m.p. 185°–187°.

EXAMPLE 34

Ethyl N-(3-hydroxy-4-hydroxymethyl-2-methyl-5-pyridylmethylthiocarbonyl)glycinate Step A: Preparation of ethyl N-(2,2,8-trimethyl-4H-1,3-dioxino[4,5-c]pyridin-5-yl methylthiocarbonyl)-glycinate To a well stirred mixture of 20 ml. of 12.5% phosgene in benzene and 50 ml. of benzene was added dropwise a solution of 2.5 gm. (0.01 moles) of 5-mercaptomethyl-2,2,8-trimethyl-4H-1,3-dioxino[4,5-c]pyridine in 25 ml. of benzene. The reaction mixture was stirred for 3 hours and then purged with nitrogen for 1 hour to remove any unreacted phosgene. The reaction mixture was then concentrated in vacuo to give a gummy solid. To the above was added 5.6 gm. (0.04 moles) of ethyl glycinate and 100 ml. of dry dioxane. The mixture was stirred and 6 ml. of triethylamine added. After stirring overnight at room temperature, the mixture was concentrated in vacuo and the residue extracted between ether and saturated sodium bicarbonate solution. The ether layer was separated, washed with water, dried over sodium sulfate and concentrated to give 4.4 gm. crude product. Chromatography on 900 gm. of silica gel and elution with ether gave 1.5 gm. of ethyl N-(2,2,8-trimethyl-4H-1,3-dioxino[4,5-c]pyridin-5-yl methylthiocarbonyl)-glycinate, m.p. 156°-158°.

Step B: Preparation of ethyl N-(3-hydroxy-4-hydroxymethyl-2-methyl-5-pyridylmethylthiocarbonyl)glycinate To 0.250 gm. of ethyl N-(2,2,8-trimethyl-4H-1,3-dioxino[4,5-c]pyridin-5-yl methylthiocarbonyl)glycinate was added enough ice cold concentrated hydrochloric acid to give 1 ml. of solution. The mixture was stirred 3 minutes in an ice bath and 3 minutes at ambient temperature and was then neutralized by the addition of saturated sodium bicarbonate solution. A gummy precipitate ormed which gradually crystallized. The solid was separated by filtration and recrystallized first from isopropanol:water then from ethyl acetate to give 0.05 gm. of ethyl N-(3-hydroxy-4-hydroxymethyl-2-methyl-5-pyridylmethylthiocarbonyl)glycinate, m.p. 147°-149°.

EXAMPLE 35

N,N'-Diethyl-2,2,8-trimethyl-4H-1,3-dioxino[4,5-c]pyridin-5-yl methylsulfenamide To a suspension of 9.5 gm. of lead thiocyanate in 200 ml. of dry ether which had been cooled to 0°-5°, was added dropwise 3.7 gm. of bromine dissolved in 25 ml. of carbon tetrachloride. The reaction mixture was stirred for 30 minutes after the addition was complete. The supernatant containing the thiocyanogen was decanted into a 1 liter flask equipped with a mechanical stirrer and ether was added to make 500 ml. of solution. A solution of 4.5 gm. of 5-mercaptomethyl-2,2,8-trimethyl-4H-1,3-dioxino[4,5-c]pyridine in 50 ml. of ether was added dropwise. A heavy precipitate formed immediately and the reaction mixture was stirred for 30 minutes after the addition was complete. Diethylamine (15 ml.) was then added and the reaction mixture allowed to come to room temperature. After 1 hour 200 ml. of benzene and 250 ml. of saturated sodium bicarbonate were added. The organic layer was separated, washed with water, dried over sodium sulfate and concentrated to give 5.5 gm. of an oil. Chromatography on 600 gm. of silica gel and elution with 50% ether in petroleum ether gave 3.2 gm. of N,N-diethyl-2,2,8-trimethyl-4H-1,3-dioxino[4,5-c]pyridin-5-yl methylsulfenamide as an oil.

EXAMPLE 36

5-Dimethylaminocarbonylthiomethyl-3-hydroxy-2-methyl-4-pyridylmethyl dimethylcarbamate To a mixture of 7.4 gm. (0.04 m) of 3-hydroxy-4-hydroxymethyl-5-mercaptomethyl-2-methylpyridine in 50 ml. dry pyridine and 50 ml. of chloroform is added dropwise with stirring a solution of 6.5 gm. (0.6 m) of dimethylcarbamoyl chloride in 50 ml. of chloroform.

The reaction mixture was stirred for 3 hours after the addition was completed, then concentrated in vacuo. The residue was extracted between ether-benzene 1:1 and saturated sodium bicarbonate solution. The organic phase was separated, washed well with water, dried over sodium sulfate, and concentrated in vacuo to give 7.2 gm. crude material. Chromatography on 900 gm. of silica gel gave 1.4 gm. of 5-dimethylaminocarbonylthiomethyl-3-hydroxy-2-methyl-4-pyridylmethyl dimethylcarbamate.

EXAMPLE 37

S,S'-Bis(3-hydroxy-4-hydroxymethyl-2-methyl-5-pyridylmethyl) 1,4-piperazinedicarbothioate dihydrochloride dihydrate Step A: Preparation of S,S'-Bis(2,2,8-trimethyl-4H-1,3-dioxino[4,5-c]pyridin-5-ylmethyl) 1,4-piperazinedicarbothioate To a solution of 4.50 gm. (0.02 m) of 5-mercaptomethyl-2,2,8-trimethyl-4H-1,3-dioxino[4,5-c]pyridine in 50 ml. of pyridine and 50 ml. of chloroform was added all at once as a solid 2.1 gm. (0.01 m) of N,N'-dichlorocarbonyl piperazine. The reaction mixture was then stirred at room temperature for 4 hours, concentrated in vacuo and extracted between chloroform and saturated sodium bicarbonate solution. The aqueous layer is separated and extracted two times with chloroform. The combined chloroform extracts were washed with water, dried and concentrated to an oil which gradually crystallized. Recrystallization from methanol gave 3.4 gm. of S,S'-bis(2,2,8-trimethyl-4H-1,3-dioxino[4,5-c]pyridin-5-yl-methyl) 1,4-piperazinedicarbothioate.

Step B: Preparation of S,S'-Bis(3-hydroxy-4-hydroxymethyl-2-methyl-5-pyridylmethyl) 1,4-piperazinedicarbothioate dihydrochloride dihydrate One hundred milligrams of S,S'-bis(2,2,8-trimethyl-4H-1,3-dioxino[4,5-c]pyridin-5-ylmethyl) 1,4-piperazinedicarbothioate is dissolved in 0.5 ml. of concentrated hydrochloric acid. After 5 minutes enough ethanol is added to make 3 ml. of solution. The resulting precipitate is filtered, washed with cold ethanol, and dried to give 0.06 gm. of S,S'-bis(3-hydroxy-4-hydroxymethyl-2-methyl-5-pyridylmethyl) 1,4-piperazine dicarbothioate dihydrochloride dihydrate.

EXAMPLE 38 o-Carboxyphenyl 3-Hydroxy-4-hydroxymethyl-2-methylpyridin-5-ylmethyl Disulfide

To a solution of 0.02 moles of o-carboxyphenyl o-carboxybenzenethiolsulfonate in 200 ml. of 95% ethanol is added 0.02 moles of fine powdered 3-hydroxy-4-hydroxymethyl-5-mercaptomethyl-2-methylpyridine. The reaction mixture is stirred overnight at room temperature and the resulting precipitate filtered to yield o-carboxyphenyl 3-hydroxy-4-hydroxymethyl-2-methylpyridin-5-ylmethyl disulfide.

EXAMPLE 39

S,S'-bis[2-methyl-3-hydroxy-4-hydroxymethyl-5-pyridylmethyl]-1,3-Propylenedicarbothioate Employing the procedure of Example 33, but substituting for the isophthaloyldichloride used therein, an equivalent amount of glutaroyl chloride, there is produced S,S'-bis[2-methyl-3-hydroxy-4-hydroxymethyl-5-pyridylmethyl]-1,3-propylenedicarbothioate.

Similarly, by employing oxalyl chloride, malonoyl chloride, succinoyl chloride or pentane dicarbonyl chloride, there are produced respectively:

S,S'-bis[2-methyl-3-hydroxy-4-hydroxymethyl-5-pyridylmethyl]-dicarbothioate

S,S'-bis[2-methyl-3-hydroxy-4-hydroxymethyl-5-pyridylmethyl]methylenedicarbothioate
S,S'-bis[2-methyl-3-hydroxy-4-hydroxymethyl-5-pyridylmethyl]-1,2-ethylenedicarbothioate, and
S,S'-bis[2-methyl-3-hydroxy-4-hydroxymethyl-5-pyridylmethyl]-1,5-pentamethylenedicarbothioate.

EXAMPLE 40

2-Methyl-3-hydroxy-4-hydroxymethyl-5-ethoxycarbonylmethylthiomethylpyridine hydrochloride Step A: Preparation of 5-carboethoxymethylthiomethyl-2,2,8-trimethyl-4H-1,3-dioxino[4,5-C]pyridine To 0.01 mole of sodium hydride in 50 ml. dry dimethylformamide under nitrogen at 0.5° is added dropwise a solution of 0.01 mole of 5-mercaptomethyl-2,2,8-trimethyl-4H-1,3-dioxino[4,5-C]pyridine in 10 ml. of dimethylformamide. When the evolution of hydrogen has ceased, 0.011 mole of ethyl bromoacetate is added. The reaction mixture is allowed to stir overnight at room temperature and then poured into a mixture of benzene-ice water. The organic layer is separated and washed well with water, dried and concentrated in vacuo. Chromatography on silica gel and elution with ether petroleum ether (10–75%) gives 5-carboethoxymethylthiomethyl-2,2,8-trimethyl-4H-1,3-dioxino[4,5-C]pyridine.

Step B: Preparation of 2-methyl-3-hydroxy-4-hydroxymethyl-5-ethoxycarbonylmethylthiomethylpyridine hydrochloride A mixture of 1.0 g. of the compound from Step A, 6.0 ml. of 2.5 N hydrochloric acid and 10 ml. of water is heated at 50° C. for 45 minutes. The mixture is made alkaline with solid sodium bicarbonate and concentrated to dryness. The residue is extracted with 50 ml. of hot isopropanol. The extract is cooled to 0° C., saturated with dry hydrogen chloride and concentrated to dryness. The solid residue is isolated by tritaration with ether and filtration and dried to give 2-methyl-3-hydroxy-4-hydroxymethyl-5-ethoxycarbonylmethylthiomethylpyridine hydrochloride.

Example 41

2-Methyl-3-hydroxy-4-hydroxymethyl-5-(2-amino-2-carboxyethylthiomethyl)pyridine hydrochloride Employing the procedure of Example 40 but substituting for the ethyl bromoacetate used therein, an equivalent amount of β-chloroalanine, there is produced 2-methyl-3-hydroxy-4-hydroxymethyl-5-(2-amino-2-carboxyethylthiomethyl)pyridine hydrochloride.

EXAMPLE 42

Bis [2-methyl-3-hydroxy-4-hydroxymethylpyridyl-5-methyl]-trisulfide

To 0.01 mole of sodium hydride in 50 ml. dry dimethylformamide under nitrogen at 0°–5° C. is added 0.01 mole of 5-mercaptomethyl-2,2,8-trimethyl-4H-1,3-dioxino[4,5-C]pyridine in 10 ml. of dimethylformamide. When the evolution of hydrogen has ceased, 0.005 mole of sulfur dichloride is added. The reaction mixture is stirred overnight, poured into benzene-ice water. The organic phase is separated, washed well with water, dried and concentrated. Chromatography on silica gel and elution with ether petroleum ether (10–80%) gives bis[2,2,8-trimethyl-4H-1,3-dioxino[4,5-C]pyridyl-5-methyl]trisulfide.

The above material is heated at 50° C. for 1 hour in 100 ml. of 2.5 N hydrochloric acid. The mixture is cooled and made alkaline with sodium bicarbonate. The precipitate is collected, washed with water and dried to give bis[2-methyl-3-hydroxy-4-hydroxymethylpyridyl-5-methyl]trisulfide.

EXAMPLE 43

Bis[2-methyl-3-hydroxy-4-hydroxymethylpyridyl-5-methyl]-tetrasulfide

Employing the procedure of Example 42 but substituting for the sulfur dichloride used therein an equivalent amount of sulfur monochloride, there is produced bis[2-methyl-3-hydroxy-4-hydroxymethylpyridyl-5-methyl]tetrasulfide.

EXAMPLE 44

3,4α-Di-O-isopropylidine derivative of 2-methyl-3-hydroxy-4-hydroxymethyl-5-mercaptomethylpyridine-N-oxide Step A: Preparation of 3,4α-di-O-isopropylidine derivative of 2-methyl-3-hydroxy-4-hydroxymethyl-5-pyridylmethylisothiuronium chloride, N-oxide 3,4α-di-O-isopropylidine derivative of 2-methyl-3-hydroxy-4-hydroxymethyl-5-chloromethylpyridine-N-oxide (5.0g.), 2.0 g. of thiourea and 60 ml. of isopropanol are refluxed under nitrogen for 2 hours. After cooling, the 3,4α-di-O-isopropylidine derivative of 2-methyl-3-hydroxy-4-hydroxymethyl-5-pyridylmethylisothiuronium chloride, N-oxide (5.7 g.) is collected by filtration.

Step B: Preparation of 3,4α-di-O-isopropylidine derivative of 2-methyl-3-hydroxy-4-hydroxymethyl-5-mercaptomethylpyridine-N-oxide The product from Step A is added to 6 g. sodium hydroxide in 60 ml. of water and heated to 80° C. for 30 minutes. Acetic acid (8 ml.) is added and the solution is partitioned between chloroform and sodium bicarbonate solution. The organic layer is separated, dried, filtered, and evaporated to give 3,4α-di-O-isopropylidine derivative of 2-methyl-3-hydroxy-4-hydroxymethyl-5-mercaptomethylpyridine-N-oxide, m.p. 138°–140° C.

EXAMPLE 45

3,4α-Di-O-isopropylidine derivative of 2-methyl-3-hydroxy-4-hydroxymethyl-5-mercaptomethylpyridine-N-oxide Step A: Preparation of 3,4α-di-O-isopropylidine derivative of sodium 2-methyl-3-hydroxy-4-hydroxymethylpyridyl-5-methylphosphorothioate, N-oxide The 3,4α-di-O-isopropylidine derivative of 2-methyl-3-hydroxy-4-hydroxymethyl-5-chloromethylpyridine-N-oxide (0.95 g.) in 25 ml. of methanol is treated with 0.54 g. of Na$_3$SPO$_3$ at room temperature. Ten ml. of water is added and precipitated monosodium salt is collected.

Step B: 3,4α-di-O-isopropylidine derivative of 2-methyl-3-hydroxy-4-hydroxymethyl-5-mercaptomethylpyridine-N-oxide The product from Step A is dissolved in 100 ml. of 2.5 N sodium hydroxide at 100° C. and stirred 10 minutes. The aqueous solution is filtered and the 3,4α-di-O-isopropylidine derivative of 2-methyl-3-hydroxy-4-hydroxymethyl-5-mercaptomethylpyridine-N-oxide is collected by filtration, m.p. 138°-140° C.

Examples 46-52 inclusive describe the preparation of the compound of structural formula

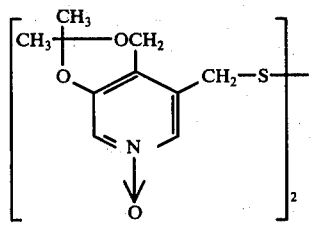

EXAMPLE 46

The 3,4α-di-O-isopropylidine derivative of ethyl 2-methyl-3-hydroxy-4-hydroxymethylpyridyl-5-methylxanthogenate N-oxide (40 g.) in 800 ml. of ethanol and 400 ml. of concentrated ammonium hydroxide is stored 5 days at room temperature. After concentrating to 50 ml., the title compound is isolated by filtration, m.p. 217°-219° C.

EXAMPLE 47

The 3,4α-di-O-isopropylidene derivative of ethyl 2-methyl-3-hydroxy-4-hydroxymethylpyridyl-5-methylxanthogenate N-oxide (36.5 g.) in 730 ml. methanol and 365 ml. concentrated ammonium hydroxide is treated with 190 ml. of 3% hydrogen peroxide dropwise over 30-45 minutes. After stirring at 2°-5° C. for 2 hours, the solvent is evaporated to give the desired product, m.p. 217°-219° C.

EXAMPLE 48

The 3,4α-di-O-isopropylidene derivative of 2-methyl-3-hydroxy-4-hydroxymethylpyridyl-5-methylisothiuronium chloride N-oxide (77.8 g.) and 27 g. of sodium tetrathionate in 500 ml. of water is treated with 350 ml. of 4 N sodium hydroxide. After 30 minutes acetic acid is added to pH 6 and precipitated product is collected by filtration, m.p. 217°-219° C.

EXAMPLE 49

The 3,4α-di-O-isopropylidene derivative of 2-methyl-3-hydroxy-4-hydroxymethyl-5-chloromethylpyridine-N-oxide (18.7 g.) in 200 ml. of methanol is treated dropwise with 70 ml. of sodium trithiocarbonate with stirring. The mixture is refluxed 20 hours, and adjusted to pH 6 with acetic acid. The desired product is collected by filtration, m.p. 217°-219° C.

EXAMPLE 50

Step A: Preparation of 3,4α-di-O-isopropylidene derivative of 2-methyl-3-hydroxy-4-hydroxymethylpyridyl-5-methylthiosulfuric acid N-oxide The 3,4α-di-O-isopropylidene derivative of 2-methyl-3-hydroxy-4-hydroxymethyl-5-chloromethylpyridine N-oxide (10 g.) is dissolved in 200 ml. of aqueous methanol (1:1 v/v) and treated with 10 g. of sodium thiosulfate in 10 ml. of water. After standing overnight at 15° C., the precipitated product is isolated by filtration.

Step B: The solid product from Step A in 200 ml. of aqueous methanol (1:1 v/v) is treated with 3.6 g. Na₂S in 10 ml. water. The precipitate is collected by filtration, washed and dried to give the desired product, m.p. 217°-219° C.

EXAMPLE 51

The product of Example 50 Step A (12.2 g.) in 200 ml. of aqueous methanol (1:1 v/v) is added to 6.35 g. of iodine in 100 ml. of methanol. The mixture is stored 40 hours. The precipitated product is isolated by filtration, washing and drying, m.p. 217°-219° C.

EXAMPLE 52

The product from Example 50 Step A (3.3 g.) in 40 ml. of 60% aqueous methanol (1:1 v/v) is treated dropwise with 0.85 g. of Na₂S₂ in 5 ml. water at room temperature over 3 hours. After 12 more hours, the precipitated disulfide product is collected on a filter, washed and dried, m.p. 217°-219° C.

Following the procedure of Example 52 but substituting for the starting material used therein an equivalent amount of the 3,4α-di-O-isopropylidene derivative of 2-methyl-3-hydroxy-4-hydroxymethyl-5-chloromethylpyridine-N-oxide, there is also produced the desired product, m.p. 217°-219° C.

In place of the chloromethyl compound in the above example, similar results are obtained by using in its place the corresponding methanesulfonyloxymethyl, toluenesulfonyloxymethyl, or benzenesulfonyloxymethyl compounds.

EXAMPLE 53

3,4α-Di-O-isopropylidene derivative of 2-methyl-3-hydroxy-4-hydroxymethyl-5-mercaptomethylpyridine-N-oxide Employing the product of Examples 46-52 in the procedure described in Example 19 Step B for the reduction of the xanthate with lithium borohydride, there is produced 3,4α-di-O-isopropylidene derivative of 2-methyl-3-hydroxy-4-hydroxymethyl-5-mercaptomethylpyridine-N-oxide, m.p. 141°-142° C.

EXAMPLE 54

3,4α-Di-O-isopropylidene derivative of 2-methyl-3-hydroxy-4-hydroxymethyl-5-mercaptomethylpyridine-N-oxide The product of Examples 46-52 (0.1 mole) in 100 ml. of methanol is treated with 5% palladium on carbon catalyst and hydrogenated unit 0.1 mole of hydrogen is consumed. The catalyst is removed by filtration and the solvent is evaporated to give 3,4α-di-O-isopropylidene derivative of 2-methyl-3-hydroxy-4-hydroxymethyl-5-mercaptomethylpyridine-N-oxide, m.p. 141°-142° C.

EXAMPLE 55

Bis(3-ethoxycarbonyloxy-4-ethoxycarbonyloxymethyl-2-methylpyridyl-5-methyl)disulfide To a mixture of 1.85 g. bis (3-hydroxy-4-hydroxymethyl-2-methylpyridyl-5-methyl)disulfide, 25 ml. of pyridine and 100 ml. chloroform which has been cooled to 0°-5° C. is added dropwise 5 ml. of ethylchloroformate. The mixture is then stirred overnight at room temperature, concentrated in vacuo, and taken up between benzene and saturated sodium bicarbonate. The aqueous layer is separated and extracted again with benzene. The combined benzene extracts are washed well with water, dried over sodium sulfate, and concentrated in vacuo to give 2.9 g. crude product. Chromatography of the latter on 200 g. silica gel and elution with ether gives 2.3 g. of product. Preparation of the HCl salt: To a solution of 0.21 g. of the above free base in 1.5 cc. of isopropanol which has been cooled to 0°–5° C. is added 0.2 cc. of concentrated hydrochloric acid. The hydrochloride salt precipitates and enough ether is added to make a total volume of 4 cc. Filtration gives 0.20 g. of bis(3-ethoxycarbonyloxy-4-ethoxycarbonyloxymethyl-2-methylpyridyl-5-methyl)disulfide dihydrochloride dehydrate, m.p. 140°–142° C.

Employing, in place of the ethylchloroformate used in the above example, other $C_{1-5}$ alkyl chloroformates or $C_{2-5}$ alkenyl chloroformates, there are produced the corresponding $C_{1-5}$ alkylcarbonates and $C_{2-5}$ alkenylcarbonates.

Similarly, Examples 56 through 72 apply equally well to the preparation of $C_{1-5}$ alkyl and $C_{2-5}$ alkenyl carbonate derivatives of 5-mercaptopyridoxine and its disulfide, bonifen.

EXAMPLE 56

Bis(3-ethoxycarbonyloxy-4-ethoxycarbonyloxymethyl-2-methylpyridyl-5-methyl)disulfide To a solution of 0.1 mole of 3-ethoxycarbonyloxy-4-ethoxycarbonyloxymethyl-5-mercaptomethyl-2-methylpyridine in dilute hydrochloric acid (100 cc.) at 0° C. is added slowly 0.1 mole of hydrogen peroxide (as a 30% solution). The reaction mixture is stirred for 5 hours and poured into a mixture of benzene and saturated sodium bicarbonate solution. The organic layer is separated, washed well with water, dried and concentrated to give bis(3-ethoxycarbonyloxy-4-ethoxycarbonyloxymethyl-2-methylpyridyl-5-methyl)disulfide.

Employing the above procedure but substituting for the starting material used therein an equivalent amount of 2-methyl-3-hydroxy-4-ethoxycarbonyloxymethyl-5-mercaptomethylpyridine, there is produced bis[2-methyl-3-hydroxy-4-ethoxycarbonyloxymethylpyridyl-5-methyl]disulfide.

Other oxidizing agents that may be employed in place of hydrogen peroxide in the above example are air or oxygen being bubbled through a solution of the mercaptan in an organic solvent; a per-acid such as m-chloroperbenzoic acid, peracetic acid, perphthalic acid, and iodine.

EXAMPLE 57

Bis(3-ethoxycarbonyloxy-4-ethoxycarbonyloxymethyl-2-methylpyridyl-5-methyl)disulfide To a mixture of 0.1 mole of bis(3-hydroxy-4-hydroxymethyl-2-methylpyridyl-5-methyl)disulfide in 50 ml. of pyridine and 150 ml. of chloroform at 0°–5° C. is added 0.4 moles of the ethyl ester of 1-chloro-N-phenyl formimidic acid. The reaction mixture is stirred for 5 hours and then concentrated in vacuo. The residue is then stirred for 3 hours in 150 ml. of 6 N hydrochloric acid. Treatment then with sodium bicarbonate gives bis(3-ethoxycarbonyloxy-4-ethoxycarbonyloxymethyl-2-methylpyridyl-5-methyl)disulfide.

Example 58

Bis(3-ethoxycarbonyloxy-4-ethoxycarbonyloxymethyl-2-methylpyridyl-5-methyl)disulfide

Step A: Preparation of 2-methyl-3-ethoxycarbonyloxy-4-ethoxycarbonyloxymethyl-5-chloromethylpyridine hydrochloride To a solution of 0.1 mole of 3-ethoxycarbonyloxy-4-ethoxycarbonyloxymethyl-5-hydroxymethyl-2-methylpyridine in 200 ml. of benzene is added dropwise with stirring and cooling 0.15 moles of thionyl chloride. The reaction mixture is stirred for 1 hour and then filtered to give 5-chloromethyl-3-ethoxycarbonyloxy-4-ethoxycarbonyloxymethyl-2-methylpyridine hydrochloride.

Step B: Preparation of 2-methyl-3-ethoxycarbonyloxy-4-ethoxycarbonyloxymethylpyridyl-5-methylthiosulfuric acid Employing the product of Step A in the procedure of Example 50 Step A, there is produced 2-methyl-3-ethoxycarbonyloxy-4-ethoxycarbonyloxymethylpyridyl-5-methylthiosulfuric acid.

Step C: Preparation of bis(3-ethoxycarbonyloxy-4-ethoxycarbonyloxymethyl-2-methylpyridyl-5-methyl)disulfide The product from Step B is then taken up in 1 N sulfuric acid and refluxed 18 hours. This is concentrated to dryness. The residue is taken up in isopropanol, extracted with sodium bicarbonate solution, washed, dried and evaporated to dryness to give bis(3-ethoxycarbonyloxy-4-ethoxycarbonyloxymethyl-2-methylpyridyl-5-methyl)disulfide.

EXAMPLE 59

Bis(3-ethoxycarbonyloxy-4-ethoxycarbonyloxymethyl-2-methylpyridyl-5-methyl)disulfide The product of Example 58 Step B (0.1 mole in 200 ml. of aqueous methanol) is treated with 0.1 mole of iodine in 100 ml. methanol. After 40 hours the precipitated product is isolated by filtration.

EXAMPLE 60

Bis(3-ethoxycarbonyloxoy-4-ethoxycarbonyloxymethyl-2-methylpyridyl-5-methyl)disulfide To 0.4 mole sodium hydride in 100 ml. dry dimethylformamide is added portionwise 0.1 mole of bis(3-hydroxy-4-hydroxymethyl-2-methylpyridyl)-5-methyl)-disulfide. After the evolution of hydrogen has ceased, this reaction mixture is added to 0.5 mole of ethyl 2,2,2-trichloroethylcarbonate in 100 ml. dimethylformamide and the resulting mixture stirred overnight at room temperature. The reaction mixture is then concentrated in vacuo, treated with benzene-ether (1:1) and 5% acetic acid. The organic layer is separated, washed well with water, dried and concentrated to give bis(3-ethoxycarbonyloxy-4-ethoxycarbonyloxymethyl-2-methylpyridyl-5-methyl)disulfide.

EXAMPLE 61

2-Methyl-3-ethoxycarbonyloxy-4-ethoxycarbonyloxymethyl-5-mercaptomethylpyridine

To a mixture of 0.1 mole of bis(3-ethoxycarbonyloxy-4-ethoxycarbonyloxymethyl-2-methylpyridyl-5-methyl)disulfide in 200 ml. of ethanol and 20 ml. acetic acid is added 15 g. of zinc dust. The reaction mixture is heated on the steam bath for 3 hours, then cooled and saturated with hydrogen sulfide. The zinc sulfide is removed by filtration and the filtrate concentrated in vacuo to give 3-ethoxycarbonyloxy-4-ethoxycarbonyloxymethyl-5-mercaptomethyl-2-methylpyridine.

Example 62

2-Methyl-3-ethoxycarbonyloxy-4-ethoxycarbonyloxymethyl-5-mercaptomethylpyridine

To a solution of 0.1 mole of bis(3-ethoxycarbonyloxy-4-ethoxycarbonyloxymethyl-2-methylpyridyl-5-methyl)disulfide in 50 ml. of ethanol which has been cooled to 0°–5° C. is added 0.075 moles of sodium borohydride. The reaction mixture is stirred cold for one hour, quenched with acetic acid and taken up between benzene ether and water. The organic layer is separated, washed well with water, dried and concentrated to give 3-ethoxycarbonyloxy-4-ethoxycarbonyloxymethyl-5-mercaptomethyl-2-methylpyridine.

EXAMPLE 63

2-Methyl-3-ethoxycarbonyloxy-4-ethoxycarbonyloxymethyl-5-mercaptomethylpyridine

A mixture of 0.1 mole of bis(3-ethoxycarbonyloxy-4-ethoxycarbonyloxymethyl-2-methylpyridyl-5-methyl)-disulfide and 25 ml. of mercaptoethanol is stirred overnight at room temperature. The reaction mixture is concentrated in vacuo and taken up between benzene-ether (1:1) and water. The organic layer is separated, washed well with water, dried and concentrated to give 3-ethoxycarbonyloxy-4-ethoxycarbonyloxymethyl-5-mercaptomethyl-2-methylpyridine.

EXAMPLE 64

2-Methyl-3-ethoxycarbonyloxy-4-ethoxycarbonyloxymethyl-5-mercaptomethylpyridine

A solution of 0.1 mole of bis(3-ethoxycarbonyloxy-4-ethoxycarbonyloxymethyl-2-methylpyridyl-5-methyl)-disulfide in 150 ml. of ethanol containing 2 g. of 10% Pd/C is reduced at 45 pounds of hydrogen pressure. When the uptake of hydrogen has ceased, the reaction mixture is filtered and the filtrate concentrated in vacuo to give 3-ethoxycarbonyloxy-4-ethoxycarbonyloxymethyl-5-mercaptomethyl-2-methylpyridine.

EXAMPLE 65

2-Methyl-3-ethoxycarbonyloxy-4-ethoxycarbonyloxymethyl-5-mercaptomethylpyridine

A solution of 0.1 mole of bis(3-ethoxycarbonyloxy-4-ethoxycarbonyloxymethyl-2-methylpyridyl-5-methyl)-disulfide in 250 ml. of 1 N hydrochloric acid is electrolyzed with a mercury cathode and a platinum anode at 20 ma and 33 v. When the reaction is complete, the addition of saturated sodium bicarbonate gives 3-ethoxycarbonyloxy-4-ethoxycarbonyloxymethyl-5-mercaptomethyl-2-methylpyridine.

EXAMPLE 66

2-Methyl-3-ethoxycarbonyloxy-4-ethoxycarbonyloxymethyl-5-mercaptomethylpyridine

A solution of 0.4 moles sodium in absolute dimethylformamide is saturated by passing in hydrogen sulfide for 5 hours. There is then added in portions 0.05 moles of 2-methyl-3-ethoxycarbonyloxy-4-ethoxycarbonyloxymethyl-5-chloromethylpyridine and the mixture stirred overnight at room temperature with hydrogen sulfide slowly bubbling through the mixture. The reaction mixture is then concentrated in vacuo and taken up between ethyl acetate and water containing acetic acid. The ethyl acetate layer is removed, dried over sodium sulfate and concentrated to give 2-methyl-3-ethoxycarbonyloxy-4-ethoxycarbonyloxymethyl-5-mercaptomethylpyridine.

EXAMPLE 67

2-Methyl-3-ethoxycarbonyloxy-4-ethoxycarbonyloxymethyl-5-mercaptomethylpyridine

The product from Example 58 Step B (0.1 mole) is added to 100 ml. of 1 N sulfuric acid with nitrogen bubbling through the mixture. After 4 hours on the steam bath, the mixture is cooled and concentrated to dryness to give 2-methyl-3-ethoxycarbonyloxy-4-ethoxycarbonyloxymethyl-5-mercaptomethylpyridine.

EXAMPLE 68

2-Methyl-3-ethoxycarbonyloxy-4-ethoxycarbonyloxymethyl-5-mercaptomethylpyridine

2-Methyl-3-ethoxycarbonyloxy-4-ethoxycarbonyloxymethyl-5-chloromethylpyridine is converted to the corresponding ethyl xanthogenate and reduced in accordance with the procedure of Example 19 Step B to give 2-methyl-3-ethoxycarbonyloxy-4-ethoxycarbonyloxymethyl-5-mercaptomethylpyridine.

EXAMPLE 69

2-Methyl-3-hydroxy-4-hydroxymethyl-5-ethoxycarbonylthiomethylpyridine and hydrochloride salt Step A: Preparation of 5-ethoxycarbonylthiomethyl-2,2,2,8-trimethyl-4H-M-dioxino[4,5-C]pyridine To a mixture of 10 g. 5-mercaptomethyl-2,2,8-trimethyl-4H-M-dioxino[4,5-C]pyridine in 50 ml. pyridine and 150 ml. chloroform which has been cooled in an ice bath is added slowly 25 ml. of ethylchloroformate. The reaction is stirred at room temperature for 1½ hours, then concentrated in vacuo. The residue is taken up between etherbenzene (1:1) and saturated sodium bicarbonate solution. The organic layer is separated, washed well with water, dried and concentrated. The residue is chromatographed on 700 g. silica gel. Elution with 50% ether in petroleum ether gives 12.5 g. of 5-ethoxycarbonylthiomethyl-2,2,8-trimethyl-4H-M-dioxino[4,5-C]pyridine which, when dissolved in ether and treated with gaseous hydrogen chloride gives the corresponding hydrochloride salt.

Step B: Preparation of 2-methyl-3-hydroxy-4-hydroxymethyl-5-ethoxycarbonylthiomethylpyridine and hydrochloride salt To 2 ml. of concentrated hydrochloric acid which has been cooled to 0° C. is added 0.5 g. of 5-ethoxycarbonylthiomethyl-2,2,8-trimethyl-4H-M-dioxino[4,5-C]pyridine. The solid gradually dissolves and after 15 minutes enough ethanol is added to make a total volume of 5 ml. Upon cooling a precipitate forms which is removed by filtration, which yields 0.15 g. of 2-methyl-3-hydroxy-4-hydroxymethyl-5-ethoxycarbonylthiomethylpyridine hydrochloride, m.p. 163°–165° C.

Alternatively, the hydrolysis may be conducted as follows:

Process 1: To 6 ml. of 6 N hydrochloric acid which has been cooled to 0° C. is added 2.0 g. of 5-ethoxycarbonylthiomethyl-2,2,8-trimethyl-4H-M-dioxino[4,5-C]pyridine. After stirring for 3 hours at room temperature, the reaction mixture is poured into benzene-ether (1:1) and excess saturated sodium bicarbonate solution. The organic layer is separated, washed well with water, then stirred for 15 minutes with 1 g. silica gel. The mixture is filtered, and the filtrate is then concentrated in vacuo to give 1.3 g. of 2-methyl-3-hydroxy-4-hydroxymethyl-5-ethoxycarbonylthiomethylpyridine m.p. 126°–128° C.

The above material is dissolved in 100 ml. ether containing about 10 ml. ethanol treated with gaseous hydrogen chloride, and the resulting precipitate is collected by filtration to give 1.25 g. of the corresponding hydrochloride, m.p. 163°–165° C.

EXAMPLE 70

2-Methyl-3-hydroxy-4-hydroxymethyl-5-ethoxycarbonylthiomethylpyridine and hydrochloride salt To a solution of 0.25 moles of Bendeis salt Eto-CO-SK in 250 ml. of cold 50% ethanol is added 0.1 mole of 5-chloromethyl-2,2,8-trimethyl-4H-M-dioxino[4,5-C]pyridine. After stirring for 5 hours at 0°–10° C., 500 ml. of water is added and the resulting mixture extracted well with etherbenzene (1:1). The combined organic extracts are washed well with water, dried and concentrated to yield 5-ethoxycarbonylthiomethyl-2,2,8-trimethyl-4H-M-dioxino-[4,5-C]pyridine. Hydrolysis as described in Example 69 Step B provides the desired compound.

When 5-chloromethyl-3-hydroxy-4-hydroxymethyl-2-methylpyridine is used in place of the above halomethyl compound, the 5-ethoxycarbonylthiomethyl-3-hydroxy-4-hydroxymethyl-2-methylpyridine is obtained directly without need of the hydrolysis step.

EXAMPLE 71

2-Methyl-3-hydroxy-4-hydroxymethyl-5-ethoxycarbonylthiomethylpyridine and hydrochloride salt.

Following the procedure of Example 34 but substituting for the ethylglycinate used in Step A thereof an equivalent amount of ethyl alcohol or sodium ethoxide, followed by hydrolysis as described in Step B of Example 34, there is produced 2-methyl-3-hydroxy-4-hydroxymethyl-5-ethoxycarbonylthiomethylpyridine and hydrochloride salt, m.p. 126°–128° C.

EXAMPLE 72

2-Methyl-3-hydroxy-4-hydroxymethyl-5-ethoxycarbonylthiomethylpyridine and hydrochloride salt To a solution of 0.1 mole sodium ethoxide in 500 ml. of ethanol cooled to 10°–20° C. and under nitrogen is added 0.1 mole ethylisothiocyanate. The reaction mixture is stirred for 30 minutes after the addition is completed. There is then added portionwise 0.1 mole of 5-chloromethyl-2,2,8-trimethyl-4H-M-dioxion[4,5-C]-pyridine. The reaction mixture is stirred at room temperature (or refluxed 3 hours) overnight, after which time 200 ml. of 6 N hydrochloric acid is added. The reaction mixture is stirred 5 hours at room temperature, concentrated in vacuo, and the residence taken up between benzeneether (1:1) and excess saturated sodium bicarbonate. The organic layer is separated, washed well with water, dried and concentrated to give 2-methyl-3-hydroxy-4-hydroxymethyl-5-ethoxycarbonylthiomethylpyridine and hydrochloride salt.

Following the above procedure but using as starting material an equivalent amount of 2-methyl-3-hydroxy-4-hydroxymethyl-5-chloromethylpyridine, the same product is obtained.

EXAMPLE 73

Bis[2-methyl-3-hydroxy-4-hydroxymethylpyridyl-5-methylthio]-carbonate

A solution of 5-mercaptopyridoxine (0.1 mole) in dry tetrahydrofuran (100 ml.) is stirred at 0°–5° C. while 1-nitrophenylchloroformate (0.1 mole) in dry tetrahydrofuran (10 ml.) is run in over 1 hour. After another hour the solution is evaporated at 10° C. to 10 ml. If need be, the intermediate p-nitrophenylmonothiocarbonate of 5-mercaptopyridoxine can be isolated by filtration at this step.

Alternatively, another 0.1 mole of 5-mercaptopyridoxine can be added prior to evaporation and the tetrahydrofuran solution warmed to 40° C. Evaporation followed by extracting the dithiocarbonate into ethylacetate (3 × 100 ml.) from saturated aqueous sodium bicarbonate is followed by drying the organic layer (MgSO$_4$). The organic layer is filtered and evaporated to dryness. The crude product is chromatographed on a silica gel column 2 in. × 2 ft. using solutions of methylene chloride-methanol as eluant to give bis[2-methyl-3-hydroxy-4-hydroxymethylpyridyl-5-methylthio]carbonate.

EXAMPLE 74

Bis[2-methyl-3-hydroxy-4-hydroxymethylpyridyl-5-methylthio]carbonate

To 0.05 moles of ammonium dithiocarbamate in 300 ml. of 75% ethanol is added 0.1 mole of 5-chloromethyl-2,2,8-trimethyl-4H-M-dioxino[4,5-C]pyridine (from corresponding HCl + NaHCO$_3$). The reaction mixture is refluxed for 2 hours, cooled to room temperature and acidified with hydrochloric acid. After 3 hours at room temperature, the reaction mixture is concentrated and the residue taken up between ether-benzene and excess saturated sodium bicarbonate. The organic layer is separated, washed well with water, dried and concentrated to give bis[2-methyl-3-hydroxy-4-hydroxymethylpyridyl-5-methylthio]carbonate.

EXAMPLE 75

Bis[2-methyl-3-hydroxy-4-hydroxymethylpyridyl-5-methylthio]-carbonate

To 0.2 mole of sodium hydride in dry dimethylformamide under nitrogen is added with cooling 0.2 moles of 5-mercaptomethyl-2,2,8-trimethyl-4H-M-dioxino[4,5-C]pyridine in dimethylformamide. The mixture is stirred for 15 minutes after the evolution of hydrogen ceases. There is then added 0.1 mole of phenylisonitrile dichloride. The reaction mixture is stirred at room temperature overnight and then concentrated in vacuo. The residence is stirred for 3 hours at room temperature in dilute hydrochloric acid. Treatment with saturated sodium bicarbonate then gives bis[2-methyl-3-hydroxy-4-hydroxymethylpyridyl-5-methylthio]carbonate.

EXAMPLE 76

Bis[2-methyl-3-hydroxy-4-hydroxymethylpyridyl-5-methylthio]carbonate

To 0.1 mole of sodium ethoxide in 150 ml. of ethanol is added 0.1 mole of 5-mercaptomethyl-2,2,8-trimethyl- 4H-M-dioxiono[4,5-C]pyridine. After 15 minutes the ethanol is removed by concentration in vacuo. To the resulting sodium mercaptide is added 0.05 mole of diphenylcarbonate and the resulting mass heated on the steam bath for 1 hour. After cooling to room temperature a mixture of benzene-ether and dilue sodium hydroxide is added. The organic layer is separated, washed well with water, dried and concentrated to give bis[2-methyl-3-hydroxy-4-hydroxymethylpyridyl-5-methylthio]carbonate.

EXAMPLE 77

Bis[2-methyl-3-hydroxy-4-hydroxymethylpyridyl-5-methylthio]-carbonate

To 0.4 mole of red mercuric oxide which is suspended by vigorous stirring in 200 ml. of water is added 0.22 moles of bis]2,2,8-trimethyl-4H-M-dioxino[4,5-C]pyridyl-5-methylthio)thiocarbonate in 100 ml. of acetic anhydride. The reaction mixture is stirred at ambient temperature for 1 hour and then extracted with ether-benzene (1:1). The organic layer is separated, washed with saturated sodium bicarbonate solution, water, dried over sodium sulfate to give bis(2,2,8-trimethyl-4H-M-dioxino[4,5-C]pyridyl-5-methylthio)carbonate. Acid hydrolysis under the usual conditions gives bis[2-methyl-3-hydroxy-4-hydroxymethylpyridyl-5-methyl-thio]carbonate.

Alternatively, the isopropylidene group can be hydrolyzed first followed by oxidation of the thiocarbonate group to the carbonate and thereby achieve the same result.

EXAMPLE 78

Bis[2-methyl-3-hydroxy-4-hydroxymethylpyridyl-5-methylthio]carbonate

A mixture of 0.1 mole of 2,2,8-trimethyl-4H-M-dioxino[4,5-C]pyridyl-5-methylthiocyanate and 5 ml. of sulfuric acid is heated slowly on the steam bath. A vigorous evolution of carbon dioxide takes place. After the evolution of gas ceases, the reaction mixture is poured onto ice and stirred for 3 hours at room temperature. This mixture is then poured into a mixture of ether-benzene and excess sodium bicarbonate solution. The organic layer is separated, washed well with water, dried and concentrated to give bis[2-methyl-3-hydroxy-4-hydroxymethylpyridyl-5-methiothio]carbonate.

EXAMPLE 79

Bis(8methyl-2-oxo-4H-M-dioxino[4,5-C]pyridyl-5-methyl)disulfide

To a mixture of 0.01 mole of bis-(3-hydroxy-4-hydroxymethyl)-2-methylpyridyl-(5)-methyldisulfide in 50 ml. chloroform and 50 ml. pyridine is added at 0°–5° C. a solution of 0.022 moles of phosgene in benzene. The reaction mixture is allowed to warm to room temperature and is stirred overnight. The reaction mixture is then concentrated in vacuo and excess saturated sodium bicarbonate solution is added. The resulting solid is collected by filtration. Chromatography on silica gel and elution with methanol in chloroform (1–5%) gives bis(8-methyl-2-oxo-4H-M-dioxino[4,5-C]pyridyl-5-methyl)disulfide.

EXAMPLE 80

Bis(8-methyl-2-oxo-4H-M-dioxino[4,5-C]pyridyl-5-methyl)-disulfide

To a mixture of 0.2 mole of bis(3-hydroxy-4-hydroxymethyl-2-methylpyridyl-5-methyl)disulfide in 100 ml. of pyridine and 300 ml. of chloroform cooled to 0°–5° C. is added 0.1 mole of phenylisonitrile dichloride in 25 ml. of chloroform. The reaction mixture is stirred for 3 hours at room temperature and then concentrated in vacuo. The resulting crude bis(8-methyl-2-phenylimino-4H-M-dioxino[4,5-C]pyridyl-5-methyl)disulfide is treated with dilute hydrochloric acid for 3 hours. Treatment of the reaction mixture with sodium bicarbonate gives bis(8-methyl-2-oxo-4H-M-dioxino[4,5-C]pyridyl-5-methyl)disulfide.

EXAMPLE 81

Bis(8-methyl-2-oxo-4H-M-dioxino[4,5-C]pyridyl-5-methyl)disulfide

A mixture of 0.1 mole of bis(3-hydroxy-4-hydroxymethyl)-2-methylpyridyl-5-methyldisulfide and 0.25 moles of ethylcarbonate containing 100 mg. of sodium ethoxide is heated at reflux and the ethanol formed during the reaction is removed by distillation. The reaction mixture is then poured into a mixture of ether-benzene and water containing 1% acetic acid. The organic layer is separated, washed well with water, dried and concentrated in vacuo to give bis(8-methyl-2-oxo-4H-M-dioxino[4,5-C]pyridyl-5-methyl)disulfide.

EXAMPLE 82

Bis(8-methyl-2-oxo-4H-M-dioxino[4,5-C]pyridyl-5-methyl(disulfide

Step A: Preparation of 5-chloromethyl-8-methyl-2-oxo-4H-M-dioxino[4,5-C]pyridine hydrochloride To a solution of 0.01 mole of 2-methyl-3-hydroxy-4-hydroxymethyl-5-chloromethylpyridine in 50 ml. chloroform and 50 ml. of pyridine is added at 0°–5° C. a solution of 0.011 mole of phosgene in benzene. The mixture is allowed to warm to room temperature and is stirred overnight. The mixture is then concentrated in vacuo and excess saturated sodium bicarbonate solution is added. The precipitate is collected on a filter and sucked dry.

Step B: Preparation of 8-methyl-2-oxo-4H-M-dioxino]4,4-C]pyridine-5-methylthiosulfuric acid The product from step A is dissolved in 200 ml. of aqueous methanol (1:1 v/v) and treated wtih 0.1 ml. of sodium thiosulfate in 10 ml. of water. After standing overnight at 15° C., the precipitated product is isolated by filtration.

Step C: Preparation of 5-mercaptomethyl-8-methyl-2-oxo-4H-M-dioxino[4,5-C]pyridine hydrochloride The product from Step B (0.01 mole) is added to 50 ml. of 1 N sulfuric acid with nitrogen bubbling through it. After 4 hours on the steam with continued nitrogen purge, the mixture is cooled and concentrated to dryness to give 5-mercaptomethyl-8-methyl-2-oxo-4H-M-dioxin[4,5-C]pyridine hydrochloride.

Step D: Preparation of bis(8-methyl-2-oxo-4H-M-dioxino[4,5-C]pyridyl-5-methyl)disulfide To 0.1 mole of 5-mercaptomethyl-8-methyl-2-oxo-4H-M-dioxino[4,5-C]pyridine hydrochloride in 100 ml. of water which has been cooled to 5° C. is added dropwise 0.1 mole of hydrogen peroxide (as a 30% solution). The reaction mixture is stirred for 2 hours, then poured into a mixture of ether-benzene (1:1) and saturated sodium bicarbonate solution. The organic layer is washed with water, dried and concentrated in vacuo to give bis(8-methyl-2-oxo-4H-M-dioxino[4,5-C]pyridyl-5-methyl)disulfide.

EXAMPLE 83

Bis(8-methyl-2-oxo-4H-M-dioxino[4,5-C]pyridyl-5-methyl)disulfide

Employing the procedures of either Example 58 or 59 but using as starting material the product of Example 82 Step B, there is produced in each case bis(8-methyl-2-oxo-4H-M-dioxino[4,5-C]pyridyl-5-methyl)disulfide.

EXAMPLE 84

Bis[3-carbamyloxy-4-carbamyloxymethyl-2-methylpyridyl-5-methyl]disulfide

A mixture of 0.1 mole of bis(3-hydroxy-4-hydroxymethyl-2-methylpyridyl-5-methyl)disulfide, 1 mole of urea and 2 g. manganous acetate is heated at 135°–155° C. for 3 hours. The reaction mixture is cooled, water added and the resulting mixture extracted well with chloroform. The combined chloroform extracts are washed with water, dried and concentrated to give bis[3-carbamyloxy-4-carbamyloxymethyl-2-methylpyridyl-5-methyl]disulfide.

EXAMPLE 85

Bis[3-carbamyloxy-4-carbamyloxymethyl-2-methylpyridyl-5-methyl]disulfide

To 2 moles of phosgene in 500 ml. chloroform at 0° C. is added 0.1 mole of bis(3-hydroxy-4-hydroxymethyl-2-methylpyridnyl-5-methyl)disulfide. After 1 hours nitrogen is bubbled through the reaction mixture to remove excess phosgene from the reaction mixture. Ammonia is then bubbled through the reaction mixture until the reaction is complete. The reaction mixture is then washed well with water and concentrated to yield bis[3-carbamyloxy-4-carbamyloxymethyl-2-methylpyridyl-5-methyl]disulfide.

EXAMPLE 86

Bis[3-carbamyloxy-4-carbamyloxymethyl-2-methylpyridyl-5-methyl]disulfide

To a stirred mixture of 0.1 mole of bis(3-hydroxy-4-hydroxymethyl-2-methylpyridyl-5-methyl)disulfide and 1 mole of sodium cyanate in 400 ml. of chloroform is added 1.1 mole of trifluoroacetic acid. The reaction mixture is stirred for 5 hours, washed well with water, dried and concentrated to give bis[3-carbamyloxy-4-carbamyloxymethyl-2-methylpyridyl-5-methyl]disulfide.

EXAMPLE 87

Bis[3-carbamyloxy-4-carbamyloxymethyl-2-methylpyridyl-5-methyl]disulfide

A mixture of 0.1 mole bis (3-hydroxy-4-hydroxymethyl-2-methylpyridyl-5-methyl)disulfide, 1 mole ethyl carbamate and 0.01 mole of aluminum isopropoxide in 200 ml. of toluene is heated and the ethanol-toluene azeotrope which forms is removed by distillation. The reaction mixture is then concentrated in vacuo, taken up between chloroform and water. The chloroform layer is separated, washed well with water, dried and concentrated to give bis[3-carbamyloxy-4-carbamyloxymethyl-2-methylpyridyl-5-methyl]-disulfide.

EXAMPLE 88

Bis[3-carbamyloxy-4-carbamyloxymethyl-2-methylpyridyl-5-methyl]disulfide

To a stirred solution of bonifen (1.97 g, 5.35 mmole) in dry pyridine (140 ml.) and chloroform (140 ml.) at 0°–5° C. is added slowly dimethylcarbamoyl chloride (15 g., 140 mmole) over a period of ½ hour. The mixture is stirred at room temperature overnight. The reaction solution is concentrated in vacuo and redissolved in chloroform (200 ml.). The chloroform layer is washed with water (2 × 200 ml.), brine (50 ml.) and dried (Na$_2$SO$_4$). The solvent is removed in vacuo to give the crude product (4.8 g.). Careful chromatography on silica gel (200 g., Baker) by eluting with 2–6% methanol in chloroform gives the desired product (600 mg.) as a glass:

Anal. Calc. for $C_{28}H_{40}N_6O_8S_2 \cdot 2HCl$ (m.p. 190°–193° C.) C, 46.34; H, 5.83; N, 11.58; Cl, 9.77; S, 8.84. Found C, 45.94; H, 5.58; N, 11.67; Cl, 9.67; S, 8.92.

Using carbamylchloride in place of dimethylcarbamylchloride gives bis[3-carbamyloxy-4-carbamyloxymethyl-2-methylpyridyl-5-methyl]disulfide.

EXAMPLE 89

Bis[3-carbamyloxy-4-carbamyloxymethyl-2-methylpyridyl-5-methyl]disulfide

Step A: Preparation of 2-methyl-3-carbamyloxy-4-carbamyloxymethyl-5-chloromethylpyridine To a stirred solution of 2-methyl-3-hydroxy-4-hydroxymethyl-5-chloromethylpyridine (0.005 mole) in 140 ml. pyridine and 140 ml. of chloroform at 0°–5° C. is added slowly carbamoyl chloride (7.5 g.) over a period of ½ hour. The mixture is stirred at room temperature overnight. The solution is concentrated in vacuo and redissolved in 200 ml. of chloroform. The chloroform is washed with 2 × 200 ml. water and dried over anhydrous sodium sulfate. The solvent is removed in vacuo to give crude 2-methyl-3-carbamyloxy-4-carbamyloxymethyl-5-chloromethylpyridine.

Step B: Preparation of 2-methyl-3-carbamyloxy-4-carbamyloxymethylpyridyl-5-methylthiosulfuric acid The product from Step A is dissolved in 200 ml. of aqueous methanol (1:1 v/v) and treated with 0.005 mole of sodium thiosulfate in 10 ml. of water. After standing overnight at 15° C., the precipitated product is isolated by filtration.

Step C: Preparation of 2-methyl-3-carbamyloxy-4-carbamyloxymethyl-5-mercaptomethylpyridine The product from Step B is added to 50 ml. of 1 N sulfuric acid with nitrogen bubbling through it. After 4 hours on the steam bath with continued nitrogen purge, the mixture is cooled and concentrated to dryness to give 2-methyl-3-carbamyloxy-4-carbamyloxymethyl-5-mercaptomethylpyridine.

Step D: Preparation of bis[3-carbamyloxy-4-carbamyloxymethyl-2-methylpyridyl-5-methyl]disulfide Following the procedure of Example 82 Step D, but substituting for the starting material therein an equivalent amount of the product from Example 89 Step C, there is produced bis[3-carbamyloxy-4-carbamyloxymethyl-2-methylpyridyl-5-methyl]disulfide.

EXAMPLE 90

Bis[3-carbamyloxy-4-carbamyloxymethyl-2-methylpyridyl-5-methyl]disulfide

Employing the procedure of either Example 58 or 59 but using as starting material the product of Example 89 Step B, there is produced in each case bis[3-carbamyloxy-4-carbamyloxymethyl-2-methylpyridyl-5-methyl]disulfide.

EXAMPLE 91

2-Methyl-3-carbamyloxy-4-carbamyloxymethyl-5-mercaptopyridoxine

Employing any of the procedures of Examples 61 through 65 but substituting as starting material therein an equivalent amount of bis[2-methyl-3-carbamyloxy-4-carbamyloxymethylpyridyl-5-methyl]disulfide, there is produced in each case 2-methyl-3-carbamyloxy-4-carbamyloxymethyl-5-mercaptopyridoxine.

EXAMPLE 92

Bis[4-carbamyloxymethyl-3-hydroxy-2-methylpyridyl-5-methyl]disulfide

Step A: Preparation of bis[4-bromomethyl-3-hydroxy-2-methylpyridyl-5-methyl]disulfide dihydrobromide A mixture of 0.1 mole of 0.1 mole of bis(3-hydroxy-4-hydroxymethyl-2-methylpyridyl-5-methyl)disulfide and 50 ml. of hydrogen bromide (48%) in acetic acid are stirred at room temperature for 5 hours. The reaction mixture is poured into ether and the resulting precipitate filtered off to give bis[4-bromomethyl-3-hydroxy-2-methylpyridyl-5-methyl]disulfide dihydrobromide.

Step B: Preparation of bis[4-carbamyloxymethyl-3-hydroxy-3-methylpyridyl-5-methyl]disulfide To 0.25 mole of silver carbamate in 100 ml. of dry dimethylformamide is added 0.1 mole of bis(4-bromomethyl-3-hydroxy-2-methylpyridyl-5-methyl)disulfide (from neutralization of the corresponding hydrobromide salt). The reaction mixture is stirred for 5 hours at room temperature, then concentrated in vacuo. The residue is taken up between chloroform and water, the chloroform layer separated, washed well with water, dried and concentrated to give bis[4-carbamyloxymethyl-3-hydroxy-2-methylpyridyl-5-methyl]disulfide.

EXAMPLE 93

Bis[4-carbamyloxymethyl-3-hydroxy-2-methylpyridyl-5-methyl]disulfide

To a stirred solution of bonifen tetraethylcarbonate (180 mg.) in methanol is passed through a stream of ammonia gas at 5°–10° C. for 15 minutes and then at 10°–20° C. for 1 hour. The reaction solution is concentrated in vacuo to a glass (170 mg.). The crude product is purified via silica gel preparative thin layer chromatography to give 60 mg. of bis[4-carbamyloxymethyl-3-hydroxy-2-methylpyridyl-5-methyl]disulfide as a glass. The dihydrochloride has m.p. 224°–227° C.

EXAMPLE 94

Sodium(2-methyl-3-hydroxy-4-hydroxymethylpyridyl-5-methyl)trithiocarbonate

2-Methyl-3-hydroxy-4-hydroxymethyl-5-chloromethylpyridine (20 g.) is suspended in water/methanol (100: 25 v/v) and treated with disodium trithiocarbonate (33%) (45 g.). The mixture is stirred at 50° C. for 4 hours under nitrogen and adjusted to pH 6.2–6.5 with dilute acid. The precipitate is recrystallized from DMF/water to give sodium (2-methyl-3-hydroxy-4-hydroxymethylpyridyl-5-methyl)trithiocarbonate.

EXAMPLE 95

Bis[2-methyl-3-hydroxy-4-hydroxymethylpyridyl-5-methyl]trithiocarbonate

To a solution of 2-methyl-3-hydroxy-5-chloromethyl-4-hydroxymethylpyridine (9 g.) in methanol (100 ml.) is added 22% sodium trithiocarbonate (17.5 ml.) at 20° C. The mixture is kept at 20° C. for 3 hours. The precipitate is collected, washed with water and hot ethanol, and dried and recrystallized from DMF to give bis[2-methyl-3-hydroxy-4-hydroxymethylpyridyl-5-methyl]trithiocarbonate.

EXAMPLE 96

Bis[3-ethoxycarbonyl-4-ethoxycarbonyloxymethyl-2-methylpyridyl-5-methyl]disulfide

Step A: Preparation of 3-ethoxycarbonyloxy-4-ethoxycarbonyloxymethyl-3-isothioureidomethyl-2-methylpyridine dihydrochloride A mixture of 0.1 mole of 5-chloromethyl-3-ethoxycarbonyloxy-4-ethoxycarbonyloxymethyl-2-methylpyridine hydrochloride, 0.11 mole of thiourea are refluxed 2 hours in 100 ml. isopropanol. The reaction mixuture is cooled and 3-ethoxycarbonyloxy-4-ethoxycarbonyloxymethyl-3-isothioureidomethyl-2-methylpyridine dihydrochloride is separated by filtration.

Step B: Preparation of bis[3-ethoxycarbonyl-4-ethoxycarbonyloxymethyl-2-methylpyridyl-5-methyl]disulfide To a solution of 0.1 mole of 3-ethoxycarbonyloxy4-ethoxycarbonyloxymethyl-5-isothioureidomethyl-2-methylpyridine in 100 ml. ethanol at 0° C. is added 0.11 mole of hydrogen peroxide (as 30% solution). After 4 days at room temperature, the mixture is concentrated in vacuo, taken up in benzene-ether (1:1), washed well with water, dried and concentrated to give bis[3-ethoxycarbonyl-4-ethoxycarbonyloxymmethyl-2-methylpyridyl-5-methyl]disulfide.

Employing the procedure of Example 96 Steps A and B but substituting for the starting material used in Step A thereof an equivalent amount of 2-methyl-3-carbamyloxy-4-carbamyloxymethyl-5-chloromethylpyridine hydrochloride, or 5-chloromethyl-8-methyl-2-oxo-4H-M-dioxino[4,5-C]pyridine hydrochloride, there is produced respectively:

bis[2-methyl-3-carbamyloxy-4-carbamyloxymethylpyridyl-5-methyl]disulfide, and
bis[8-methyl-2-oxo-4H-M-dioxino[4,5-C]pyridine-5-methyl]disulfide.

EXAMPLE 97

3-Ethoxycarbonyloxy-4-ethoxycarbonyloxymethyl-5-mercaptomethyl-2-methylpyridine

Step A: Preparation of sodium (3-ethoxycarbonyloxy-4-ethoxycarbonyloxymethyl-2-methylpyridyl-5-methyl)trithiocarbonate To a mixture of 0.1 mole of 5-chloromethyl-3-ethoxycarbonyloxy-4-ethoxycarbonyloxymethyl-2-methylpyridine in 100 ml. of 50% methanol is added 0.1 mole of disodium trithiocarbonate. The reaction mixture is stirred at 50° C. for 5 hours under nitrogen, then concentrated in vacuo to give sodium (3-ethoxycarbonyloxy-4-ethoxycarbonyloxymethyl-2-methylpyridyl-5-methyl)trithiocarbonate.

Step B: Preparation of 3-ethoxycarbonyloxy-4-ethoxycarbonyloxymethyl-5-mercaptomethyl-2-methylpyridine The above material is dissolved in 50 ml. of 1 N hydrochloric acid and stirred under nitrogen for 1 hour. The reaction mixture is then poured into ether-benzene (1:1) and saturated sodium bicarbonate. The organic layer is separated, washed well with water, dried and concentrated to give 3-ethoxycarbonyloxy-4-ethoxycarbonyloxymethyl-5-mercaptomethyl-2-methylpyridine.

Following the procedure of Example 97 Steps A and B but substituting for the starting material used therein an equivalent amount of 2-methyl-3-carbamyloxy-4-carbamyloxymethyl-5-chloromethylpyridine or 5-chloromethyl-8-methyl-2-oxo-4H-dioxino[4,5-C]pyridine, there is produced respectively:

2-methyl-3-carbamyloxy-4-carbamyloxymethyl-5-mercaptomethylpyridine, and
5-mercaptomethyl-8-methyl-2-oxo-4H-m-dioxino-[4,5-c]pyridine.

EXAMPLE 98

5-Mercaptomethyl-8-Methyl-2-Oxo-4H-m-Dioxino[4,5-c]pyridine

Step A: Preparation of 5-chloromethyl-2-oxo-4H-m-dioxino[4,5-c]pyridine

To a mixture of 0.01 mole of 2-methyl-3-hydroxy-4-hydroxymethyl-5-chloromethylpyridine in 50 ml. chloroform and 50 ml. pyridine is added at 0°–5° C. a solution of 0.011 moles of phosgene in benzene. The reaction mixture is allowed to warm to room temperature and is stirred overnight. The reaction mixture is then concentrated in vacuo and excess saturated sodium bicarbonate solution is added. The resulting solid is collected by filtration. Chromatography on silica gel and elution with methanol in chloroform (1-5%) gives 5-chloromethyl-8-methyl-2-oxo-4H-m-dioxino[4,5-c]pyridine.

Step B: Preparation of 8-methyl-2-oxo-4H-m-dioxino[4,5-c]pyridyl-5-methylthiosulfuric acid The product from Step A is dissolved in 200 ml. of aqueous methanol (1:1 v/v) and treated with 10 g. of sodium thiosulfate in 10 ml. of water. After standing overnight at 15° C., the precipitated product is isolated by filtration.

Step C: Preparation of 5-mercaptomethyl-8-methyl-2-oxo-4H-m-dioxino[4,5-c]pyridine The product from Step B is added to 100 ml. of 1 N sulfuric acid with nitrogen bubbling through it. After 4 hours on the steam bath, the mixture is cooled and concentrated to dryness to give 5-mercaptomethyl-8-methyl-5-oxo-4H-m-dioxino[4,5-c]pyridine.

EXAMPLE 99

5-Mercaptomethyl-8-Methyl-2-Oxo-4H-m-Dioxino[4,5-c]pyridine

Employing the procedure substantially as described in Example 66, but substituting for the starting material therein, an equivalent amount of the product from Example 98, there is produced 5-mercaptomethyl-3-methyl-2-oxo-4H-m-dioxino[4,5-c]pyridine.

EXAMPLE 100

5-Mercaptomethyl-8-Methyl-2-Oxo-4H-m-Dioxino[4,5-c]pyridine

5-Chloromethyl-8-methyl-2-oxo-4H-m-dioxino-[4,5-c]pyridine is converted to the corresponding ethyl xanthogenate and reduced in accordance with the procedure of Example 19, Step B, to give 5-mercaptomethyl-8-methyl-2-oxo-4H-m-dioxino[4,5-c]pyridine.

EXAMPLE 101

5-Mercaptomethyl-8-Methyl-2-Oxo-4H-m-Dioxino[4,5-c]-pyridine

Employing any one of the procedures substantially as described in Examples 61 through 65, but substituting for the starting material used therein an equivalent amount of bis[8-methyl-2-oxo-4H-m-dioxino[4,5-c]pyridyl-5-methyl]disufide, there is produced in each case 5-mercaptomethyl-8-methyl-2-oxo-4H-m-dioxino[4,5-c]pyridine.

EXAMPLE 102

2-Methyl-3-Carbamyloxy-4-Carbamyloxymethyl-5-Mercaptomethyl Pyridine

Step A: Preparation of 2-methyl-3-carbamyloxy-4-carbamyloxymethyl-5-chloromethylpyridine To a stirred solution of 2-methyl-3-hydroxy-4-hydroxymethyl-5-chloromethylpyridine (5.35 m mole) in dry pyridine (140 ml.) and chloroform (140 ml.) at 0°–5° C. is added slowly carbamoyl chloride (70 mmole) over a period of ½ hour. The mixture is stirred at room temperature overnight. The reaction solution is concentrated in vacuo and redissolved in chloroform (200 ml.). The chloroform layer is washed with water (2 × 200 ml.), brine (50 ml.) and dried ($Na_2SO_4$). The solvent is removed in vacuo to give the crude product. Careful chromatography on silica gel (200 g., Baker) by eluting with 2-6% methanol in chloroform gives the desired product.

Step B: Preparation of 2-methyl-3-carbamyloxy-4-carbamyloxymethylpyridine-5-methylthiosulfuric acid The product from Step A is dissolved in 200 ml. of aqueous methanol (1:1 v/v) and treated with 10 g. sodium thiosulfate in 10 ml. water. After standing overnight at 15° C., the precipitated product is isolated by filtration.

Step C: Preparation of 2-methyl-3-carbamyloxy-4-carbamyloxymethyl-5-mercaptomethylpyridine The product from Step B is added to 100 ml. of 1 N sulfuric acid with nitrogen bubbling through it. After 4 hours on the steam bath, the mixture is cooled and concentrated to dryness.

EXAMPLE 103

2-Methyl-3-Carbamyloxy-4-Carbamyloxymethyl-5-Mercaptomethylpyridine

Employing the procedure substantially as described in Example 66, but substituting for the starting material therein, an equivalent amount of the product from Example 102, there is produced 2-methyl-3-carbamyloxy-4-carbamyloxymethyl-5-mercaptomethylpyridine.

EXAMPLE 104

2-Methyl-3-Carbamyloxy-4-Carbamyloxymethyl-5-Mercaptomethylpyridine

2-Methyl-3-carbamyloxy-4-carbamyloxymethyl-5-chloromethylpyridine is converted to the corresponding ethylxanthogenate and reduced in accordance with the procedure of Example 19, Step B, to give 2-methyl-3-carbamyloxy-4-carbamyloxymethyl-5-mercaptomethylpyridine.

EXAMPLE 105

2-Methyl-3-Ethoxycarbonyloxy-4-Hydroxymethyl-5-Mercaptomethylpyridine

Step A: Preparation of 4-acetoxybut-2-enol 0.1 Mole of 1,4-dihydroxy-but-2-one is stirred in anhydrous pryidine (100 ml.) while 0.1 mole of acetic anhydride is added in pyridine (10 ml.) dropwise over 1 hour. The reaction mixture is evaporated to dryness and extracted from saturated sodium bicarbonate with 2 × 100 ml. of chloroform. The combined chloroform layers are then washed with 2.5 N hydrochloric acid (2 × 25 ml.) and water (20 ml.).

The chloroform layer is dried and filtered. The solvent is evaporated and the residue fractionally distilled under reduced pressure. The intermediately distilling fraction is the title compound.

Step B: Preparation of 4-acetoxybut-2-enyl chloride 0.1 Mole of the above compound is stirred in dry thionyl chloride (100 ml.) containing 0.01 ml. of dry dimethylformamide overnight at 0° C. The solvents are evaporated off and the crude product is used in the next reaction.

Step C: Preparation of 4-mercapto-but-2-enol

The above compound in B (0.1 mole) is refluxed with thiourea (0.11 mole) in methanol for 30 mins. The crude product is isolated by partial evaporation of the methanol and filtration. The solid thioureido derivative is stirred in 1:1 aqueous alcoholic 2.5 N sodium hydroxide solution (40 ml.) for 2 hours under $N_2$. The solution is acidified with 2.5 N hydrochloric acid under $N_2$ and the alcohol evaporated off under $N_2$. The aqueous solution is extracted with ethyl acetate (4 × 50 ml.). The ethyl acetate dried and the solvent evaporated to give 4-mercapto-but-2-enol which is purified by fractional distillation under $N_2$.

Step D: Preparation of 2,2-dimethyl-4,7-dihydro-1,3-thioxepine

The product from Reaction C above (0.1 mole) is stirred for 2 hours under $N_2$ with acetone (200 ml.) and saturated at 20° C. with gaseous hydrogen chloride. At the end of this time the acetone solution is evaporated to dryness and the product purified by fractional distillation.

Step E: Preparation of 4,5-o,s-isopropylidene-5-mercaptopyridoxine 0.1 Mole of 4-methyl-5-ethoxyoxazole, 2 moles of the thioxepine D, 0.1 gm. of copper powder, 0.1 gm. glass powder and 0.02 gm. N,N-dimethylaniline are heated in a sealed tube at 170°–250° for 8 hours. The solution is filtered and the thioxepine distilled off. The residual oil is chromatographed on silica gel to obtain pure 4,5-o,s-isopropylidene-5-mercaptopyridoxine.

Step F: Preparation of 3-ethoxycarbonyl-4,5-di o,s-isopropylidene-5-mercaptopyridoxine A solution of the 4,5-o,s-diisopropylidene compound (0.1 mole) in 100 ml. of dry tetrahydrofuran (50 ml.) and dry pyridine (10 ml.) is stirred at room temperature and ethyl chloroformate (20%) excess is run in in 10 ml. dry tetrahydrofuran over 10 min. After 1 hour the solution is evaporated to 5 ml. and extracted into ethyl acetate (100 ml.). The ethyl acetate solution is washed with water (3 × 10 ml.), separated and dried. The filtered solution is chromatographed on silica gel to give a pure fraction of 2-ethoxycarbonyl-4,5-di o,s-isopropylidene-5-mercaptopyridoxine.

Step C: Preparation of 3-ethyl carbonate of 5-mercaptopyridoxine

The above product (0.2 gm.) is stood in 10 ml. of 15% hydrochloric acid overnight and then poured onto solid sodium bicarbonate. Pure 3-ethylcarbonate of 5-MP is extracted from the solution with ethyl acetate.

EXAMPLE 106

Bis[2-Methyl-3-Ethoxycarbonyloxy-4-Hydroxymethylpyridyl-5-Methyl]Disulfide

Treatment of the product from Example 105 with hydrogen peroxide, air, oxygen, a per acid or iodine as described in Example 56, produces the title compound.

Employing carbamoyl chloride and N,N-dimethylcarbamoyl chloride in place of the ethyl chloroformate used in Example 105, there are produced:

2-methyl-3-carbamyloxy-4-hydroxymethyl-5-mercaptomethylpyridine, and
2-methyl-3-N,N-dimethylcarbamyloxy-4-hydroxymethyl-5-mercaptomethylpyridine, which treatment with hydrogen peroxide, air, oxygen, a per acid, or iodine as described in Example 56, there are produced:

bis[2-methyl-3-carbamyloxy-4-hydroxymethylpyridyl-5-methyl]disulfide, and
bis[2-methyl-3-N,N-dimethylcarbamyloxy-4-hydroxymethylpyridyl-5-methyl]disulfide.

Employing the procedure of Example 105, Step E, but substituting for the 2,2-dimethyl-4,7-dihydro-1,3-thioxepine, an equivalent amount of 4-ethoxycarbonylthiobut-2-enol, there is produced 2-methyl-3-hydroxy-4-hydroxymethyl-5-ethoxycarbonylthiomethylpyridine.

Using other $C_{1-5}$ alkoxycarbonylthiobut-2-enols or $C_{2-5}$ alkenyloxycarbonylthiobut-2-enols, the corresponding alkoxycarbonyl or alkenyloxycarbonyl compounds are obtained.

Also employing the procedure of Example 105, Step E, but substituting for the 2,2-dimethyl-4,7-dihydro-1,3-thioxepine, an equivalent amount of bis[4-ethoxycarbonyloxybut-2-enyl]disulfide, there is produced bis[2-methyl-3-hydroxy-4-ethoxycarbonyloxymethylpyridyl-5-methyl]disulfide.

Similarly prepared are the 4-$C_{1-5}$ alkoxycarbonyloxy methyl- and 4-$C_{2-5}$ alkenyloxycarbonyloxymethyl compounds.

EXAMPLE 107

A mixture of 250 parts of Compound I and 25 parts of lactose is granulated with suitable water, and to this is added 100 parts of maize starch. The mass is passed through a 16 mesh screen. The granules are dried at a temperature below 60° C. The dry granules are passed through a 16 mesh screen, and mixed with 3.8 parts of magnesium stearate. They are then compressed into tablets suitable for oral administration.

The specific mercaptomethylpyridine used in the foregoing example may be replaced by 25, 100, 250, or 500 parts of other mercaptomethylpyridines of this invention to produce tablets suitable for oral administration according to the method of this invention.

EXAMPLE 108

A mixture of 50 parts of Compound II, 3 parts of the calcium salt of lignin sulfonic acid, and 237 parts of water is ball-milled until the size of substantially all of the particles is less than 10 microns. The suspension is diluted with a solution containing 3 parts of sodium carboxymethylcellulose and 0.9 parts of the butyl ester of p-hydroxybenzoic acid in 300 parts of water. There is thus obtained an aqueous suspension suitable for oral administration for therapeutic purposes.

EXAMPLE 109

A mixture of 250 parts of Compound IV, 200 parts of maize starch and 30 parts of alginic acid is mixed with a sufficient quantity of 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

EXAMPLE 110

A mixture of 500 parts Compound V, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

EXAMPLE 111

1. Tablets — 10,000 scored tablets for oral use, each containing 500 mg. of active ingredient are prepared from the following ingredients:

|  | Gm. |
| --- | --- |
| Compound VI | 5000 |
| Starch, U.S.P. | 350 |
| Talc, U.S.P. | 250 |
| Calcium stearate | 35 |

The powdered mercaptomethylpyridine is granulated with a 4% w./v. aqueous solution of methylcellulose U.S.P. (1500 cps.). To the dried granules is added a mixture of the remainder of the ingredients and the final mixture compressed into tablets of proper weight.

2. Capsules — 10,000 two-piece hard gelatine capsules for oral use, each containing 250 mg. of active ingredient are prepared from the following ingredients:

|  | Gm. |
| --- | --- |
| Compound VIII | 2500 |
| Lactose, U.S.P. | 1000 |
| Starch, U.S.P. | 300 |
| Talc, U.S.P. | 65 |
| Calcium stearate | 25 |

The powdered mercaptomethyl compound is mixed with the starch-lactose mixture followed by the talc and calcium stearate. The final mixture is then encapsulated in the usual manner. Capsules containing 10, 25, 50, and 100 mg. of active ingredient are also prepared by substituting 100, 250, 500, and 1000 gm. for 2500 gm. in the above formulation.

3. Soft elastic capsules — One-piece soft elastic capsules for oral use, each containing 500 mg. of active material are prepared in the usual manner by first dispersing the powdered active material in sufficient corn oil to render the material capsulatable.

4. Aqueous suspension — An aqueous suspension for oral use containing in each 5 ml., 1 gm. of active ingredient is prepared from the following ingredients:

|  | Gm. |
| --- | --- |
| Compound IX | 2000 |
| Methylparaben, U.S.P. | 7.5 |
| Propylparaben, U.S.P. | 2.5 |
| Saccharin sodium | 12.5 |
| Glycerin | 3000 |
| Tragacanth powder | 10 |
| Orange oil flavor | 10 |
| F.D.&C. orange dye | 7.5 |
| deionized water, q.s. to 10,000 ml. |  |

What is claimed is:
1. A compound of structural formula:

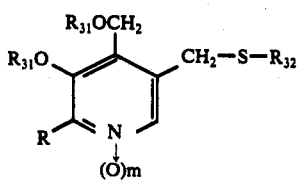

or pharmaceutically acceptable salt thereof, wherein m is 0 or 1;

R is $C_{1-5}$alkyl;

$R_{31}$ groups are the same or different and are hydrogen

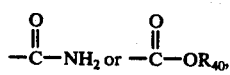

where $R_{40}$ is $C_{1-5}$alkyl or $C_{2-5}$alkenyl, $R_{32}$ is hydrogen or

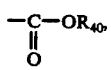

with the proviso that if both $R_{31}$ groups are hydrogen and m is 0, then $R_{32}$ is not hydrogen.

2. The compound of claim 1 of structural formula:

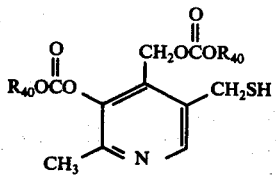

where $R_{40}$ is $C_{1-5}$alkyl or $C_{2-5}$ alkenyl or pharmaceutically acceptable salt thereof.

3. The compound of claim 1 of structural formula:

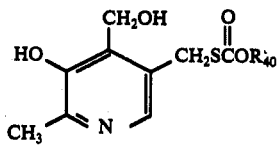

or pharmaceutically acceptable salt thereof.

4. The compound of claim 1 of structural formula:

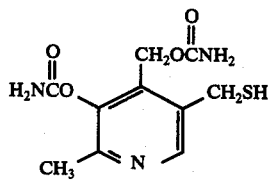

or pharmaceutically acceptable salt thereof.

5. A method of treating rheumatoid arthritis in humans and warm-blooded animals in need of such treatment which comprises the administration of from 1 mg. to 140 mg. per killogram of body weight per day of a compound of structural formula:

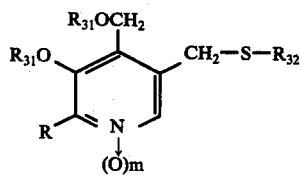

wherein m, R, $R_{31}$ and $R_{32}$ are as defined in claim 1.

6. A pharmaceutical composition in unit dosage form for the treatment of rheumatoid arthritis comprising an inert pharmaceutically acceptable carrier and from 5 mg. to 5 gm. of a compound of structural formula:

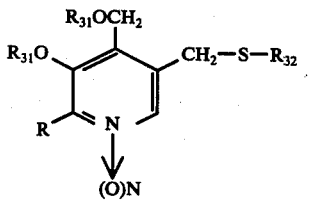

wherein m, R, $R_{31}$ and $R_{32}$ are as defined in claim 1.

* * * * *